United States Patent [19]
Orr et al.

[11] Patent Number: 5,741,645
[45] Date of Patent: Apr. 21, 1998

[54] GENE SEQUENCE FOR SPINOCEREBELLAR ATAXIA TYPE 1 AND METHOD FOR DIAGNOSIS

[75] Inventors: Harry T. Orr, Minneapolis; Laura P. W. Ranum, St. Paul; Ming-Yi Chung, Minneapolis, all of Minn.; Huda Y. Zoghbi, Houston, Tex.

[73] Assignee: Regents of the University of Minnesota, Minneapolis, Minn.

[21] Appl. No.: 469,802

[22] Filed: Jun. 6, 1995

Related U.S. Application Data

[63] Continuation of Ser. No. 84,365, Jun. 29, 1993, abandoned.

[51] Int. Cl.$^6$ .............................. C12Q 1/68; C12P 19/34; C07H 21/04
[52] U.S. Cl. .......................... 435/6; 435/91.2; 536/23.1; 536/23.5; 536/24.31; 536/24.33; 935/77; 935/78; 935/8; 935/9
[58] Field of Search ....................... 435/6, 912; 536/23.1, 536/23.5, 24.31, 24.33; 935/4, 6, 8, 9, 78, 11

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,800,159 | 1/1989 | Mullis et al. | 435/91.2 |
| 5,023,171 | 6/1991 | Ho et al. | 435/6 |

FOREIGN PATENT DOCUMENTS

| | | |
|---|---|---|
| WO 91/09140 | 6/1991 | WIPO. |
| WO 92/12262 | 7/1992 | WIPO. |
| WO 92/14840 | 9/1992 | WIPO. |
| WO 92/20825 | 11/1992 | WIPO. |
| WO 94/24279 | 10/1994 | WIPO. |

OTHER PUBLICATIONS

H.M. Albertsen, et al., "Construction and characterization of a yeast artificial chromosome library containing seven haploid human genome equivalents", *Proc. Natl. Acad. Sci. USA*, 87, 4256–4260 (1990).

S. Banfi et al., "An easy and rapid method for the detection of chimeric yeast artificial chromosome clones", *Nucleic Acids Res.*, 20, 1814 (1992).

G.P. Bates et al., "Characterization of a yeast artificial chromosome contig spanning the Huntington's disease gene candidate region", *Nature Genetics*, 1, 180–187 (1992).

H.J. Bellen et al., "The Drosophila Couch potato protein is expressed in nuclei of peripheral neuronal precursors and shows homology to RNA-binding proteins", *Genes & Development*, 6, 2125–2136 (1992).

M. Benson et al., "The Drosophila zeste protein binds cooperatively to sites in many gene regulatory regions: implications for transvection and gene regulation", *EMBO J*, 7, 3907–3915 (1988).

C. Breukel et al., "Vector–Alu PCR: a rapid step in mapping cosmids and YACs", *Nucleic Acids Res.*, 18, 3097 (1990).

S.K. Bronson et al., "Isolation and characterization of yeast artificial chromosome clones linking the HLA–B and HLA–C loci", *Proc. Natl. Acad. Sci. USA*, 88, 1676–1680 (1991).

(List continued on next page.)

*Primary Examiner*—Carla J. Myers
*Attorney, Agent, or Firm*—Mueting, Raasch, Gebhardt & Schwappach, P.A.

[57] ABSTRACT

The present invention provides an isolated DNA sequence of the short arm of chromosome 6 which is located within the autosomal dominant spinocerebellar ataxia type 1 gene. This isolated DNA sequence is preferably located within a 3.36 kb EcoRI fragment, i.e., an EcoRI fragment containing about 3360 base pairs, of the SCA1 gene. The isolated sequence preferably contains a CAG repeat region. The number of CAG trinucleotide repeats (n) is $\leq 36$, preferably n=19–36, for normal individuals. For an affected individual n>36, preferably n$\geq$43.

13 Claims, 12 Drawing Sheets

OTHER PUBLICATIONS

J.D. Brook et al., "Molecular Basis of Myotonic Dystrophy: Expansion of a Trinucleotide (CTG) Repeat at the 3' End of a Transcript Encoding a Protein Kinase Family Member", *Cell*, *68*, 799–808 (1992).

B.H. Brownstein et al., "Isolation of single-copy human genes from a library of yeast artificial chromosome clones", *Science 244*, 1348–1351 (1989).

H.G. Brunner et al., "Brief Report: Reverse mutation in Myotonic Dystrophy", *New Engl. J. Med.*, *328*, 476–480 (1993).

J. Buxton et al., "Detection of an unstable fragment of DNA specific to individuals with myotonic dystrophy", *Nature*, *355*, 547–548 (1992).

P.M. Conneally et al., "Report of the committee on methods of linkage analysis and reporting", *Cytogenet. Cell. Genet.*, *40*, 356–359 (1985).

A.J. Courey et al., "Synergistic Activation by the Glutamine-Rich Domains of Human Transcription Factor Sp1", *Cell*, *59*, 827–836 (1989).

P. Coutinho et al., "Autosomal dominant system degeneration in Portuguese families of the Azores Islands", *Neurology*, *28*, 703–709 (1978).

R.D. Currier et al., "Spinocerebellar ataxia: study of a large kindred", *Neurology*, *22*, 1040–1043 (1972).

C.A. Feener et al., "Rapid detection of CA polymorphisms in cloned DNA: Application to the 5' region of the dystrophin gene", *Am. J. Hum. Genet.*, *48*, 621–627 (1991).

A.P. Feinberg et al., "A technique for radiolabeling DNA restriction endonuclease fragments to high specific activity", *Anal. Biochem.*, *137*, 266–267 (1984).

Y.-H. Fu et al., "Variation of the CGG Repeat at the Fragile X Site Results in Genetic Instability: Resolution of the Sherman Paradox", *Cell*, *67*, 1047–1058 (1991).

Y.-H. Fu et al., "An Unstable Triplet Repeat in a Gene Related to Myotonic Muscular Dystrophy", *Science*, *255* 1256–1258 (1992).

E.D. Green et al., "Systematic screening of yeast artificial-chromosome libraries by use of the polymerase chain reaction", *Proc. Natl. Acad. Sci. USA*, *87*, 1213–1217 (1990).

J.L. Haines et al., "Spinocerebellar ataxia in large kindred: age at onset, reproduction, and genetic linkage studies", *Neurology*, *34*, 1542–1548 (1984).

H.G. Harley et al., "Expansion of an unstable DNA region and phenotypic variation in myotonic dystrophy", *Nature*, *355*, 545–546 (1992).

H.G. Harley et al., "Unstable DNA sequence in myotonic dystrophy", *Lancet*, *139*, 1125–1128 (1992).

D.M. Heery et al. "A simple method for subcloning DNA fragments from gel slices", *Trends Genet.*, *6*, 173 (1990).

Huntington's Disease Collaborative Reserach Group, "A Novel Gene Containing a Trinucleotide Repeat That is Expanded and Unstable on Huntington's Disease Chromosomes", *Cell*, *72*, 971–983 (1993).

J.F. Jackson et al., "Spinocerebellar ataxia and HLA linkage: risk prediction by HLA typing", *N. Engl. J. Med.*, *296*, 1138–1141 (1977).

G. Joslyn et al., "Identification of deletion mutations and three new genes at the familial polposis locus", *Cell*, *66*, 601–613 (1991).

B.J.B. Keats et al., "Tight Linkage of the gene for spinocerebellar ataxia to D6S89 on the short arm of chromosome 6 in a kindred for which close linkage to both HLA and F13A1 is excluded", *Am. J. Hum. Genet.*, *49*, 972–977 (1991).

E.J. Kremer et al., "Mapping of DNA Instability at the Fragile X to a Trinucleotide Repeat Sequence p(CCG)n", *Science*, *252*, 1711–1714 (1991).

T.J. Kwiatkowski et al., "Rapid identification of yeast artificial chromosome clones by matrix pooling and crude lysate PCR", *Nucleic Acids Res.*, *18*, 7191–7192 (1990).

T.J. Kwiatkowski et al., "The gene for autosomal dominant spinocerebellar ataxia (SCA1) maps centromeric to D6S89 and shows no recombination, in nine large kindreds, with a dinucleotide repeat at the AM10 locus", *Am. J. Hum. Genet.* *53*, 391–400 (1993).

A.R. LaSpada et al., "Androgen receptor gene mutations in X-linked spinal and bulbar muscular atrophy", *Nature*, *352*, 77–79 (1991).

G.M. Lathrop et al., "Strategies for multilocus linkage analysis in humans", *Proc. Natl. Acad. Sci. USA*, *81*, 3443–3446 (1984).

F. LeBorgne-Demarquoy et al., "Two dinucleotide repeat polymorphisms at the D6S202 locus", *Nucleic Acids Res.*, *19*, 6060 (1991).

M. Litt et al., "Dinucleotide Repeat Polymorphism at the D6S89 Locus", *Nucleic Acids Res.*, *18*, 4301 (1990).

M. Mahadevan et al., "Myotonic Dystrophy Mutation: An Unstable CTG Repeat in the 3' Untranslated Region of the Gene", *Science*, *255*, 1253–1255 (1992).

D. Marchuk et al., "Construction of T-vectors, a rapid and general system for direct cloning of unmodified PCR products", *Nucleic Acids Res.*, *19*, 1154 (1990).

D.L. Nelson et al., "Alu-primed polymerase chain reaction for regional assignment of 110 yeast artificial chromosome clones from the human X chromosome: Identification of clones associated with a disease locus", *Proc. Natl. Acad. Sci. USA*, *88*, 6157–6161 (1991).

D.L. Nelson et al., "Alu polymerase chain reaction: A method for rapid isolation of human-specific sequences from complex DNA sources", *Proc. Natl. Acad. Sci. USA*, *86*, 6686–6690 (1989).

NIH/CEPH Collaborative Mapping Group, "A comprehensive genetic linkage map of the human genome", *Science*, *258*, 67–86 (1992).

H.E. Nino et al., "A family with hereditary ataxia: HLA typing", *Neurology*, *30*, 12–20 (1980).

G. Orozco et al., "Dominantly inherited olivopontocerebellar atrophy from eastern Cuba", *J. Neurolog. Sciences*, *93*, 37–50 (1989).

H.T. Orr, "Molecular genetics of the SCA1 locus on chromosome 6P", Abstract of National Institute of Health Grant No. 5R01NS22920–05.

C.A. Quigley et al., "Complete Deletion of the Androgen Receptor Gene: Definition of the Null Phenotype of the Androgen Insensitivity Syndrome and Determination of Carrier Status", *J. Clin. Endo. Metab.*, *74*, 927–933 (1992).

L.P.W. Ranum et al., "Localization of the autosomal dominant, HLA-linked spinocerebellar ataxia (SCA1) locus in two kindreds within an 8cM subregion of chromosome 6p", *Am. J. Hum. Genet.*, *49*, 31–41 (1991).

L.P.W. Ranum et al., "Dinucleotide repeat polymorphism at the D6S109 locus", *Nucleic Acids Res.*, *19*, 1171 (1991).

R.K. Saiki et al., "Enzymatic Amplification of β–Globin Genomic Sequences and Restriction Site Analysis for Diagnosis of Sickle Cell Anemia", *Science*, 230, 1350–1354 (1985).

J. Sambrook et al., *Molecular Cloning, A Laboratory Manual*, 2nd ed.; Cold Spring Harbor, NY (1989). Enclosed is the Title page, Copyright page, and Contents pages (pp. v–xxxii).

S.J. Scharf et al., "Direct Cloning and Sequence Analysis of Enzymatically Amplified Genomic Sequences", *Science*, 233, 1076–1078 (1986).

J.W. Schut et al., "Hereditary ataxia: clinical study through six generations", *Arch Neurol. Psychiatry*, 63, 535–567 (1950).

D.C. Schwartz et al., "Separation of yeast chromosome-sized DNAs by pulsed field gradient gel electrophoresis", *Cell*, 37, 67–75 (1984).

P.G. Sealy et al., "Removal of repeated sequences from hybridization probes", *Nucleic Acids Res.*, 13, 1905–1922 (1985).

G.A. Silverman et al., "Use of yeast artificial chromosome clones for mapping and walking within human chromosome segment 18q21.3", *Proc. Natl. Acad. Sci. USA*, 86, 7485–7489 (1989).

M. Spadaro et al., "HLA–linked spinocerebellar ataxia: a clinical and genetic study of large Italian kindreds", *Acta Neurol. Scand.*, 85, 257–265 (1992).

M. Trifiro et al., "The 56/58 kDa androgen–binding protein in male genital skin fibroblasts with a deleted androgen receptor gene", *Molecular and Cellular Endocrinology*, 75, 37–47 (1991).

H. Vaessin et al., "prospero Is Expressed in Neuronal Precursors and Encodes a Nuclear Protein that is involved in the Control of Axonal Outgrowth in Drosophila", *Cell*, 67, 941–953 (1991).

G.J.B. Van Ommen et al., "Restriction analysis of chromosomal DNA in a size range up to two million base pairs by pulsed field graident electrophoresis" in *Human Genetic Diseases, A Practical Approach*; K.E. Davies, ed.; IRL Press, Oxford; pp. 113–133 (1986).

A.J.M.H. Verkerk et al., "Identification of a Gene (FMR–1) Containing a CGG Repeat Coincident with a Breakpoint Cluster Region Exhibiting Length Variation in Fragile X Syndrome", *Cell*, 65, 905–914 (1991).

M.C. Wapenaar et al., "The genes for X–linked ocular albinism (OA1) and microphthalmia with linear skin defects (MLS): cloning and characterization of the critical regions", *Hum. Mol. Genet.*, 2, 947–952 (1993).

J. Weissenbach et al., "A second–generation linkage map of the human genome", *Nature*, 359, 794–801 (1992).

K.A. Wharton et al., "Nucleotide Sequence from the Neurogenic Locus Notch Implies a Gene Product that Shares Homology with Proteins Containing EGF–like Repeats", *Cell*, 43, 567–581 (1985).

H. Yakura et al., "Hereditary ataxia and HLA genotypes", *N. Engl. J. Med.*, 291, 154–155 (1974).

H.Y. Zoghbi, "Molecular Studies of HLA–Linked Spinocerebellar Ataxia", Abstract of National Institute of Health Grant No. 5R01NS27699–05.

H.Y. Zoghbi, "The Spinocerebellar degenerations", in *Current Neurology*; S.H. Appel, ed.; vol. 11, pp. 121–144; Mosby–Year Book, St. Louis (1991).

H.Y. Zoghbi et al., "Deletion and linkage mapping of eight markers from the proximal short arm of chromosome 6", *Genomics*, 6, 352–357 (1990).

H.Y. Zoghbi et al., "Generation of YAC Contigs by Walking", in *YAC Libraries*; D.L. Nelson et al., eds.; W.H. Freeman & Co: New York, NY; pp. 93–112 (1993).

H.Y. Zoghbi et al., "The gene for autosomal dominant spinocerebellar ataxia (SCA1) maps telomeric to HLA complex and is closely linked to the D6S89 locus in three large kindreds", *Am. J. Hum. Genet.*, 49, 23–30 (1991).

H.Y. Zoghbi et al., "Sixty–five radiation hybrids for the short arm of human chromosome 6p: Their value as a mapping panel and as a source for rapid isolation of new problems using repeat element–mediated PCR", *Genomics*, 9, 713–720 (1991).

H.Y. Zoghbi et al., "Spinocerebellar ataxia: Variable age of onset and linkage to human leukocyte antigen in a large kindred", *Ann. Neurol.*, 23, 580–584 (1988).

H.Y. Zoghbi et al., "Assignment of autosomal dominant spinocerebellar ataxia (SCA1) centromeric to the HLA region of the short arm of chromosome 6, using multilocus linkage analysis", *Am. J. Hum. Genet.*, 44, 255–263 (1989).

A. Volz et al., "Regional Mapping of the Gene for Autosomal Dominant Spinocerebellar Ataxia (SCA1) by Localizing the Closely Linked D6S89 Locus to 6p24.2—p23.05", *Cytogenetics and Cell Genetics*, vol. 60, No. 1, 1992, pp. 37–39.

M. Chung, "Positional Cloning and Characterization of the Spinocerebellar Ataxia Type I Gene", *Dissertation Abstract International B*, vol. 54, No. 12, Jun. 1994, p. 6039–B.

H.T. Orr et al., "Expansion of an Unstable Trinucleotide CAG Repeat in Spinocerebellar Ataxia Type 1", *Nature Genetics*, vol. 4, No. 3, Jul. 1993, p. 221–226.

M. Chung et al., "Evidence for a Mechanism Predisposing to Intergenerational CAG Repeat Instability in Spinocerebellar Ataxia Type 1", *Nature Genetics*, vol. 5, No. 3, Nov. 1993, pp. 254–258.

S. Banfi et al., "Mapping and Cloning of the Critical Region for the Spinocerebellar Ataxia Type 1 Gene (SCA1) in a Yeast Artificial Chromosome Contig Spanning 1.2 Mb", *Genomics*, vol. 18, No. 3, Dec. 1993, pp. 627–635.

S. Banfi et al., "Identification and Characterization of the Gene Causing Type 1 Spinocerebellar Ataxia", *Nature Genetics*, vol. 7, No. 4, Aug. 1994, pp. 513–520.

L.P.W. Ranum et al., "Molecular and Clinical Correlations in Spinocerebellar Ataxia Type I: Evidence for Familial Effects on the Age of Onset", *Am. J. Hum. Genet.*, vol. 55, No. 2, Aug. 1994, pp. 244–252.

Sommer and Tautz, Minimal Homology Requirements for PCR Primers., (1989) p. 6749, Nucleic Acids Research.

Renauld et al., Human P40–IL–9 Expression in Activated CD4 Positive T Cell Genomic Organization and Comparison with Mouse Gene, (1990) J. Immunol., 144(11), pp. 4235–4241.

FIG. 1

```
   1  TTTTGAAACT TGCAGAGAAC AGGATTATTT CTGGCGGCCT CTGCTGAGTT GGCGTGTGTG
  61  TGTGTGTTTG TGTGTGTGTG TATTAGGGAG AGGAAATCGT AGGTCCAGTG TGGACCCAGA
 121  GCTAAGGGGA ATCTTGGAGA GTAGTGGCTC TGGCAGATGA GGATTCAGAA ATCGAGTGCA
 181  AGGACTGTTC TGGACTTTCA CTGCTAACCT GCTTTTTCTC AGTGCCTGGC TCTGAGGGCA
 241  GGGTCCAGCT GGTGTCATGC TCTCCAAGGG CTTCATTTTA TGTTCCAGCC AGGCAAAGGA
 301  GAGGTGAGAA ATGGAACCAA CATTTCTGAA AAGGAAATTT AAGAACTGCA TCATCTGCCC
 361  TTGAAGAAGA AAAGGAGAAA AAAAAACAGG AGAGAGGGTA TTGAGAACAT CTTAGGGGAG
 421  TTGTTAACTC CATTAAAAAA TATATGTGTT ACAGTGTTCA CTTGCCCAGT GTCTTCATAA
 481  TCTTCCTTTA TAATGTGCAG CTGCCACGGC TAGTGTTTTT GTTTTTGTTG TTGTTGTTTT
 541  GTTTCGTTTT TGGAGACAGA GTGTCGCTCT GTTGCCCAGG CTGGAGTACA ATGGTGCAAT
 601  CTCGGCTCAC TGCAACCTCT GCCTCCTGGG TTCAAGCAAT TCTCCTGCCT CAGCCTCTCA
 661  AGTAGCTGGG ACTACAGCCG TGTGCCAGCT AATGTTACAC CAGGCTAAAT TTGTTTTTTA
 721  TTTTTTATTT TTGGTAGAGA CGGGGTTTCA CCATGTTAGC CAGGATGGTC TTAATCTCCT
 781  GACCTCGTGA TCTGCCTGCC TCGGCCTCCC AAAGTGTTGG CTAGTGTTTT CTCTGCTTCA
 841  GTGCTTGGGG TATGATTGGG TTATGGGAGT TCACACCGAG TCCAGGGCCT AGTCTTAATC
 901  TTGCCAAAGA TGTTCTTTCC CCGGTGCTCA TGTTCTGATG TCCTTTCCCT CCTTCCCTTT
 961  CTCCTCCCTT TCCTTTTCCC TTTGTCACTG CCCTCTTCCC TTTCCCAGCA TCCAGAGCTG
1021  CTGTTGGCGG ATTGTACCCA CGGGGAGATG ATTCCTCATG AAGAGCCTGG ATCCCCTACA
1081  GAAATCAAAT GTGACTTTCC GTTTATCAGA CTAAAATCAG AGCCATCCAG AACAGTGAAA
1141  CAGTCACCGT GGAGGGGGGA CGGCGAAAAA TGAAATCCAA CCAAGAGCGG AGCAACGAAT
1201  GCCTGCCTCC CAAGAAGCGC GAGATCCCCG CCACCAGCCG GTCCTCGGAG GAGAAGGCCC
1261  CTACCCTGAC CCAGCGACAA CCACCGGGTG GAGGGCACAG CATTGGCTCC CGGGCAACCC
1321  TGGTGGCCGG GGCCACGGGG GCGGGAGGCA TGGGCCGGCA GGGACCTCGG TGGAGCTTGG
1381  TTTACAACAG GGAATAGGTT TACACAAAGC ATTGTCCACA GGGCTGGACT ACTCCCCGCC
1441  CAGCGCTCCC AGGTCTGTCC CCGTGGCCAC CACGCTGCCT GCCGCGTACG CCACCCCGCA
1501  GCCAGGGACC CCGGTGTCCC CCGTGCAGTA CGCTCACCTG CCGCACACCT TCCAGTTCAT
1561  TGGGTCCTCC CAATACAGTG GAACCTATGC CAGCTTCATC CCATCACAGC TGATCCCCCC
1621  AACCGCCAAC CCCGTCACCA GTGCAGTGGC CTCGGCGCAG GGGCCACCAC TCCATCCCAG
1681  CGCTCCCAGC TGGAGGCCTA TTCCACTCTG CTGGCCAACA TGGGCAGTCT GAGCCAGACG
1741  CCGGGACACA AGGCTGAGCA GCAGCAGCAG CAGCAGCAGC AGCAGCAGCA GCAGCATCAG
1801  CATCAGCAGC AGCAGCAGCA GCAGCAGCAG CAGCAGCAGC AGCAGCAGCA CCTCAGCAGG
1861  GCTCCGGGGC TCATCACCCC GGGTCCCCCC CAACCAGCCC AGCAGAACCA GTACGTCCAC
1921  ATTTCCAGTT CTCCGCAGAA CACCGGCCGC ACCGCCTCTC CTCCGGCCAT CCCCGTCCAC
1981  CTCCACCCCC ACCAGACGAT GATCCCACAC ACGCTCACCC TGGGGCCCCC CTCCCAGGTC
2041  GTCATGCAAT ACGCCGACTC CGGCAGCCAC TTTGTCCCTC GGGAGGCCAC CAAGAAAGCC
2101  GAGAGCAGCC GGCTGCAGCA GGCCATCCAG GCCAAGGAGG TCCTGAACGG TGAGATGGAG
2161  AAGAGCCGGC GGTACGGGGC CCCGTCCTCA GCCGACCTGG GCCTGGGCAA GGCAGGCGGC
2221  AAGTCGGTTC CTCACCCGTA CGAGTCCAGG CACGTGGTGG TCCACCCGAG CCCCTCAGAC
2281  TACAGCAGTC GTGATCCTTC GGGGGTCCGG GCCTCTGTGA TGGTCCTGCC CAACAGCAAC
2341  ACGCCCGCAG CTGACCTGGA GGTGCAACAG GCCACTCATC GTGAAGCCTC CCCTTCTACC
2401  CTCAACGACA AAAGTGGCCT GCATTTAGGG AAGCCTGGCC ACCGGTCCTA CGCGCTCTCA
2461  CCCCACACGG TCATTCAGAC CACACACAGT GCTTCAGAGC CACTCCCGGT GGACTGCCAG
2521  CCACGGCCTT CTACGCAGGG ACTCAACCCC CTGTCATCGG CTACCTGAGC GGCCAGCAGC
2581  AAGCAATCAC CTACGCCGGC AGCCTGCCCC AGCACCTGGT GATCCCCGGC ACACAGCCCC
2641  TGCTCATCCC GGTCGGCAGC ACTGACATGG AAGCGTCGGG GGCAGCCCCG GCCATAGTCA
2701  CGTCATCCCC CCAGTTTGCT GCAGTGCCTC ACACGTTCGT CACCACCGCC CTTCCCAAGA
2761  GCGAGAACTT CAACCCTGAG GCCCTGGTCA CCCAGGCCGC CTACCCAGCC ATGGTGCAGG
2821  CCCAGATCCA CCTGCCTGTG GTGCAGTCCG TGGCCTCCCC GGCGGCGGCT CCCCCTACGC
2881  TGCCTCCCTA CTTCATGAAA GGCTCCATCA TCCAGTTGGC CAACGGGGAG CTAAAGAAGG
2941  TGGAAGACTT AAAACAGAAG ATTTCATCCA GAGTGCAGAG ATAAGCAACG ACCTGAAGAT
3001  CGACTCCAGC ACCGTAGAGA GGATTGAAGA CAGCCATAGC CCGGGCGTGG CCGTGATACA
3061  GTTCGCCGTC GGGGAGCACC GAGCCCAGGT AACGTTAGCC AGGGTGGCAC AGGGATGGGA
3121  CACCATACCG TGATGCCATC ATCATCTCCT GGCAAGACGA ATTGCTTCTA TGAGGCAGGA
3181  TTAAGGGTTC TCGGGTACAC CTAGACCTTA GACTCGGCCT TTCCCAACTG CGTTCTCTAG

3241  AAAAAATAAG CCCCATTTCC CCGTGATCTC TGCTGTGTGT AATGAATTAA CCTCCATGCA
3301  TGGAGAGTGG GGCTAGTTAT GGAGTCCTTG AGACAATCCA GAAACTCACC ACTCTCGTTA
3361  TTTTTT
```

FIG. 2

Patient #1   (CAG)nCACCTCAGCAGGGCTCCGGGGCTCATC; n=56.

CAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCACCTCAGCAGGGCTCCGGGGCTCATC

Patient #2   (CAG)nCACCTCAGCAGGGCTCCGGGGCTCATC; n=69.

CAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAG
CAGCAGCAGCACCTCAGCAGGGCTCCGGGGCTCATC

Patient #3   (CAG)nCACCTCAGCAGGGCTCCGGGGCTCATC; n=47.

CAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAG
CAGCAGCAGCACCTCAGCAGGGCTCCGGGGCTCATC

Patient #4   (CAG)nCACCTCAGCAGGGCTCCGGGGCTCATC; n=48.

CAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAG
CAGCAGCAGCAGCACCTCAGCAGGGCTCCGGGGCTCATC

Patient #5   TGAG(CAG)n; n=50.

TCAGCAGCAGCAGCAGCAGCAGCAGCAGCAGCAGCAGCAGCAGCAGCAGCAGCAGCAGCAGCA
GCAGCAGCAGCAGCAGCAGCAGCAGCAGCAGCAGCAGCAGCAGCAGCAGCAGCAGCAGCAGCA
GCAGCAGCAGCAGCAGCAG

FIG. 3

```
  1  GATCCCCCCA ACCGCCAACC CCGTCACCAG TGCAGTGGCC TCGGCGCAGG
            ────GCT-435──────▶

51  GGCCACCACT CCATCCCAGC GCTCCCAGCT GGAGGCCTAT TCCACTCTGC
                                                ─────CAG-b──▶
              ──────Rep-2──▶
101  TGGCCAACAT GGGCAGTCTG AGCCAGACGC CGGGACACAA GGCTGAGCAG

151  CAGCAGCAGC AGCAGCAGCA GCAGCAGCAG CAGCATCAGC ATCAGCAGCA

◀────CAG-a─────────
201  GCAGCAGCAG CAGCAGCAGC AGCAGCAGCA GCAGCAGCAC CTCAGCAGGG
     ──────────              ◀─────GCT-214────    ◀─
251  CTCCGGGGCT CATCACCCCG GGTCCCCCCC ACCAGCCCAG CAGAACCAGT

◀──Rep-1  Pre-2──▶
301  ACGTCCACAT TTCCAGTTCT CCGCAGAACA CCGGCCGCAG CGCCTCTCCT

351  CCGGCCATCC CCGTCCACCT CCACCCCCAC CAGACGATGA TCCCACACAC

401  GCTCACCCTG GGCCCCCCT CCCAGGTCGT CATGCAATAC GCCGACTCCG

◀─── Pre-1 ──────────
451  GCAGCCACTT TGTCCCTCGG GAGGCCACCA AGAAAGCCGA GAGCAGCCGG

501  CTGCAG
```

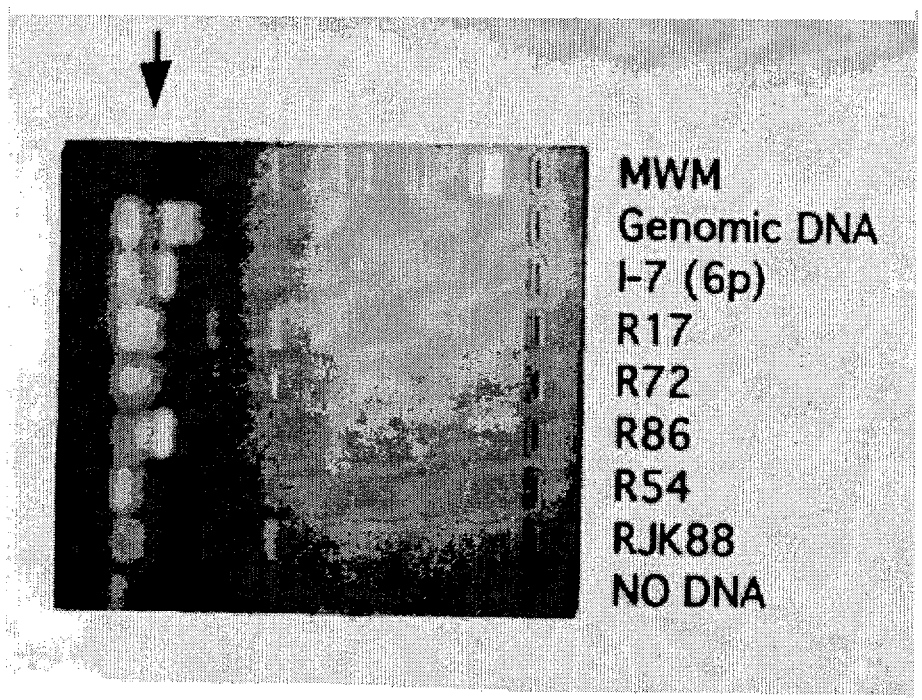
FIG. 5b
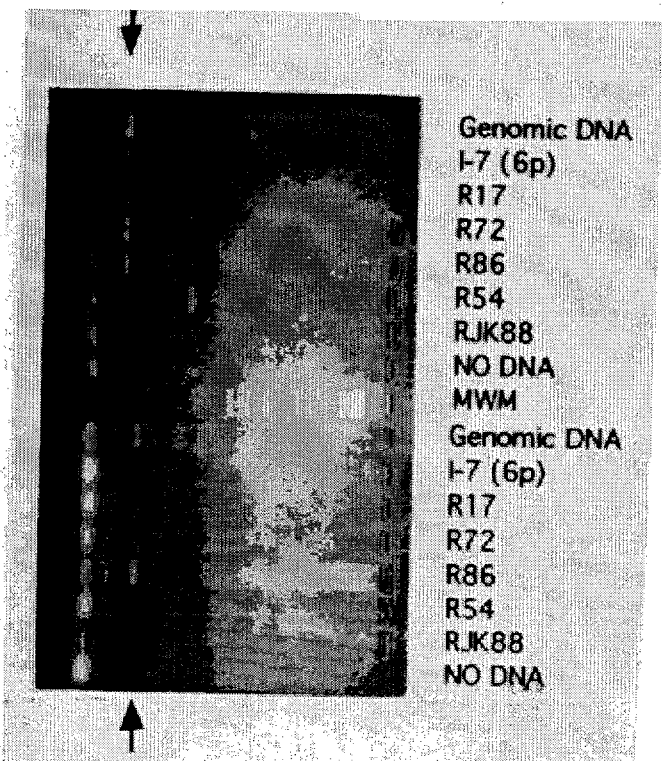

GENE SEQUENCE FOR SPINOCEREBELLAR ATAXIA TYPE 1 AND METHOD FOR DIAGNOSIS

This is a continuation of application Ser. No. 08/084,365, filed Jun. 29, 1993, abandoned.

The present invention was made with government support under Grant Nos. NS 22920 and 27699, awarded by the National Institutes of Health. The Government has certain rights in this invention.

BACKGROUND OF THE INVENTION

The spinocerebellar ataxias are a heterogeneous group of degenerative neurological disorders with variable clinical features resulting from degeneration of the cerebellum, brain stem, and spinocerebellar tracts. The clinical symptoms include ataxia, dysarthria, ophthalmoparesis, and variable degrees of motor weakness. The symptoms usually begin during the third or fourth decade of life, however, juvenile onset has been identified. Typically, the disease worsens gradually, often resulting in complete disability and death 10–20 years after the onset of symptoms. Individuals with juvenile onset spinocerebellar ataxias, however, typically have more rapid progression of the phenotype than the late onset cases. A method for diagnosing spinocerebellar ataxias would provide a significant step toward its treatment.

Spinocerebellar ataxia type 1 (SCA1) is an autosomal dominant disorder which is genetically linked to the short arm of chromosome 6 based on linkage to the human major histocompatibility complex (HLA). See, for example, H. Yakura et al., *N. Engl. J. Med.*, 291, 154–155 (1974); and J. F. Jackson et al., *N. Engl. J. Med.*, 296, 1138–1141 (1977). SCA1 has been shown to be tightly linked to the marker D6S89 on the short arm of chromosome 6, telomeric to HLA. See, for example, L. P. W. Ranum et al., *Am. J. Hum. Genet.*, 49, 31–41 (1991); and H. Y. Zoghbi et al., *Am. J. Hum. Genet.*, 49, 23–30 (1991). Recently, two families with dominantly inherited ataxia failed to show detectable linkage with HLA markers but were found to have SCA1 when studied for linkage to D6S89, demonstrating the superiority of the latter marker for study of ataxia families. See, for example, B. J. B. Keats et al., *Am. J. Hum. Genet.*, 49, 972–977 (1991). The identification and cloning of the SCA1 gene could provide methods of detection that would be extremely valuable for both family counseling and planning medical treatment.

SUMMARY OF THE INVENTION

The present invention is directed to a portion of an isolated 1.2-Mb region of DNA from the short arm of chromosome 6 containing a highly polymorphic CAG repeat region. This CAG repeat region is unstable and is expanded in individuals with the autosomal dominant neurodegenerative disorder spinocerebellar ataxia type 1. Southern and PCR analyses of the CAG repeat region demonstrate a direct correlation between the size of the expanded repeat region and the age-of-onset of the disorder, with larger alleles occurring in juvenile cases.

Specifically, the present invention provides an isolated DNA sequence of the short arm of chromosome 6. The claimed sequence is located within the autosomal dominant spinocerebellar ataxia type 1 gene (herein referred to as "SCA1"). This isolated DNA sequence is preferably located within an EcoRI fragment of the SCA1 gene, i.e., a fragment obtained through digestion with EcoRI endonuclease restriction enzyme. More preferably, the isolated sequence is a 3.36-kb EcoRI fragment, i.e., an EcoRI fragment containing about 3360 base pairs, of the SCA1 gene. The isolated sequence contains a polymorphic CAG repeat region. By this it is meant that there are repeating CAG trinucleotides in this portion of the gene that can vary in the number of CAG trinucleotides. The number of trinucleotide repeats can vary from as few as 19, for example, to as many as 81, for example.

For a normal individual, $n \leq 36$ in the $(CAG)_n$ region, and typically $n=19-36$. This region in a normal allele of the SCA1 gene is optionally interrupted with CAT trinucleotides. Typically, there are no more than about 3 CAT trinucleotides, either individually or in combination, within any $(CAG)_n$ region. The $(CAG)_n$ region of this isolated sequence is unstable. That is, this region is larger, i.e., expanded, in individuals who have symptoms of the disease, or who are likely to develop symptoms of the disease. For an affected individual, i.e., an individual with an affected allele of the SCA1 gene, $n>36$ in the $(CAG)_n$ region, and typically $n \geq 43$. The isolated DNA sequence of the SCA1 gene is about 3360 base pairs in length, and substantially corresponds to the sequence as shown in FIG. 1. The sequences of a portion of the 3.36-kb EcoRI fragment within the SCA1 gene of several affected individuals is shown in FIG. 2.

As used herein, an "affected" gene refers to the allele of the SCA1 gene that, when present in an individual, is the cause of spinocerebellar ataxia type 1, and an "affected" individual has the symptoms of autosomal dominant spinocerebellar ataxia type 1. Individuals with only "normal" copies of the SCA1 gene, do not possess the symptoms of SCA1. The term "allele" means a genetic variation associated with a coding region; that is, an alternative form of the gene.

A gene probe for identifying a DNA sequence located within the SCA1 gene is also provided. The gene probe can be used for distinguishing between the normal and the larger affected alleles of the SCA1 gene. The gene probe is a portion of a nucleotide sequence of the SCA1 gene having at least about 200 nucleotides. The nucleotide sequence preferably corresponds to the DNA sequence of an EcoRI fragment of the SCA1 gene, and more preferably a 3.36-kb EcoRI fragment of the SCA1 gene, or portion thereof. The probe can contain any portion of the 3.36-kb EcoRI fragment, including any portion of the $(CAG)_n$ region, although this is not a requirement. It is desireable, however, for the probe to contain a portion of the 3.36 kb EcoRI fragment on either side of the $(CAG)_n$ region.

The gene probe of the present invention is useable in a method of diagnosing a patient for SCA1. Thus, the diagnosis involves detecting the presence of a DNA sequence located within an SCA1 gene. Specifically, the method includes the steps of digesting genomic DNA with a restriction endonuclease to obtain DNA fragments; preferably, separating the fragments by size using gel electrophoresis; probing said DNA fragments under hybridizing conditions with a detectably labelled gene probe comprising a DNA sequence of an SCA1 gene having at least about 200 base pairs; detecting probe DNA which has hybridized to said DNA fragments; and analyzing the DNA fragments for a $(CAG)_n$ region characteristic of the normal or affected forms of the SCA1 gene.

The present invention is also directed to oligonucleotides, particularly primers for use in PCR techniques, for diagnosing the neurodegenerative disorder SCA1. The oligonucleotides include a nucleotide sequence capable of hybridizing to a portion of DNA of a 3.36 kb EcoRI fragment of an SCA1 gene having a CAG repeat region. Alternatively stated, each primer is substantially complementary to a portion of a strand of a 3.36-kb EcoRI fragment of an SCA1 gene having a CAG repeat region, i.e., a $(CAG)_n$ region. The oligonucleotide, e.g., primer, sequence has at least about 11 nucleotides, preferably at least about 16 nucleotides and no more than about 35 nucleotides. The oligonucleotides, e.g., primers, are chosen such that they produce a primed product of about 70–350 base pairs, preferably about 100–300 base pairs. More preferably, the oligonucleotides, e.g., primers, are chosen such that nucleotide sequence is complementary to a portion of a strand of an affected or a normal allele within about 150 nucleotides on either side of the $(CAG)_n$ region, including directly adjacent to the $(CAG)_n$ region. Most preferably, the primer is selected from the group consisting of CCGGAGCCCTGCTGAGGT (CAG-a) (SEQ ID NO:8), CCAGACGCCGGGACAC (CAG-b) (SEQ ID NO:9), AACTGGAAATGTGGACGTAC (Rep-1) (SEQ ID NO:10), CAACATGGGCAGTCTGAG (Rep-2) (SEQ ID NO:11), CCACCACTCCATCCCAGC (GCT-435) (SEQ ID NO:12), TGCTGGGCTGGTGGGGGG (GCT-214) (SEQ ID NO:13), CTCTCGGCTTTCTTGGTG (Pre-1) (SEQ ID NO:14), and GTACGTCCACATTTCCAGTT (Pre-2) (SEQ ID NO:15). These primers substantially correspond to those shown in FIG. 3.

They can be used in any combination for sequencing or producing amplified DNA sequences using various PCR techniques. Preferably, for amplification of the DNA sequence characteristic of SCA1, Rep-1 and Rep-2 is the primer pair used. As used herein, the term "amplified DNA sequence" refers to DNA sequences that are copies of a portion of a DNA sequence and its complementary sequence. The copies correspond in nucleotide sequence to the original DNA sequence and its complementary sequence. The term "complement", as used herein, refers to a DNA sequence that is complementary to a specified DNA sequence. The term "primer pair", as used herein, means a set of primers including a 5' upstream primer that hybridizes with the 5' end of the DNA sequence to be amplified and a 3' downstream primer that hybridizes with the complement of the 3' end of the sequence to be amplified.

Using the primers of the present invention, PCR technology can be used in the diagnosis of the neurological disorder SCA1 by detecting a region of greater than about 36 CAG repeating trinucleotides, preferably at least 43 repeating CAG trinucleotides. Generally, this involves treating separate complementary strands of the DNA sequence containing a region of repeating CAG codons with a molar excess of two oligonucleotide primers, extending the primers to form complementary primer extension products which act as templates for synthesizing the desired sequence containing the CAG repeating units, and detecting the sequence so amplified.

BRIEF DESCRIPTION OF THE DRAWINGS

FIG. 1. Sequence of the 3.36 kb EcoRI fragment of the normal SCA1 gene located within the short arm of chromosome 6. It is within this fragment that mutations occur in the CAG repeat region which are associated with autosomal dominant spinocerebellar ataxia type 1 (SEQ ID NO:1).

FIG. 2. Sequence information for five affected individuals in the CAG repeat region, i.e., the CAG trinucleotide repeat, and its flanking regions of the SCA1 gene located within a short arm of chromosome 6 (SEQ ID NO:2), (SEQ ID NO:3), (SEQ ID NO:4), (SEQ ID NO:5), and (SEQ ID NO:6).

FIG. 3. Sequence of the CAG trinucleotide repeat and its flanking regions. About 500 nucleotides in a single strand of DNA of the 3.36 kb EcoRI fragment of the SCA1 gene shown in FIG. 1 is represented. The locations of PCR primers are shown by solid lines with arrowheads (SEQ ID NO:7).

FIGS. 5A–5C. Regional localization of 6p22-23 STSs by PCR analysis of radiation reduced hybrids. Three panels (a–c) demonstrate the regional localization of D6S274, D6S288, and AM10GA. In each panel PCR amplification results are shown for genomic DNA, the I-7 cell line which retains 6p, the radiation reduced hybrids R17, R72, R86, and R54, and RJK88 hamster DNA. A blank control (c) is shown for every panel. R86 has been previously shown to retain D6S89; R17 and R72 are known to contain D6S88 and D6S108, two DNA markers which map centromeric to D6S89. An amplification product is seen in I-7, R17, R72, and R86 for D6S274 and D6S288, whereas the amplification product for AM10GA is only seen in I-7 and R86 confirming that D6S274 and D6S288 map centromeric to AM10GA and D6S89.

FIG. 10a: TaqI-digested DNA from a TX-SCA1 kindred. The unaffected spouse has a single fragment at 2830-bp. The affected individual with onset at 25 years of age has the 2830-bp fragment as well as a 2930-bp fragment. The affected child with onset at 4 years inherited the normal 2830-bp from her mother, and has a new fragment of 3000-bp not seen in either parent. FIG. 10b: TaqI-digested DNA from individuals from a MN-SCA1 kindred. The unaffected spouse and the unaffected sibling have a 2830-bp fragment. The two affected brothers have the 2830-bp fragment as well as an expanded fragment of 2900-bp in the sib with onset at 25 years and 2970-bp in the sib with onset at 9 years. FIG. 10c: BstNI-digested DNA from the TX-SCA1 kindred. Lanes 1–3 are from the same kindred depicted in (A). The normal fragment size is 530-bp, in individuals with onset at 25–30 years (lanes 1 and 4) the fragment expands to 610-bp. In the individual with onset at 15 years of age (lane 7) the fragment size is 640-bp, and in the individual with onset at 4 years (lane 3) the fragment size is 680-bp. The DNA in lane 5 is from a 14 year old child who is asymptomatic.

DETAILED DESCRIPTION

Figure 4:
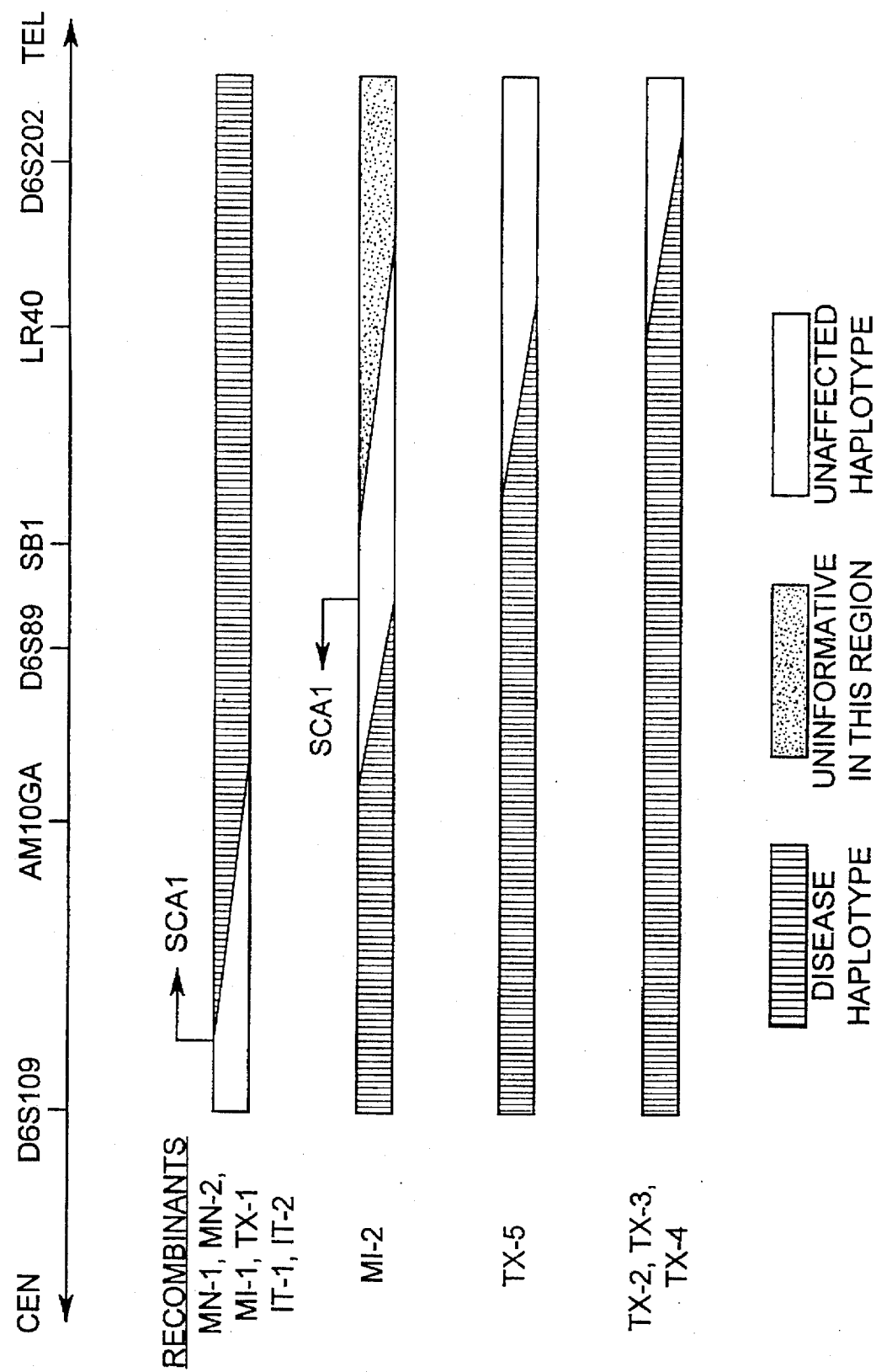
FIG. 4. Summary of SCA1 recombination events that led to the precise mapping of the SCA1 locus. Recombinant disease-carrying chromosomes are shown for the markers shown above. A schematic diagram of the relevant region of 6p22 (not drawn to scale) is shown at the top of the figure. Families are coded as follows: TX=Houston, MN=Minnesota, MI=Michigan, IT=Italy. Each recombination event is given a number following the family code.

Substantial efforts have been made to localize the SCA1 gene using genetic and physical mapping methods. Genetically, SCA1 is flanked on the centromeric side by D6S88 at a recombination fraction of approximately 0.08 (based on marker-marker distances using the Centre d'Etude du Polymorphisme Humain (CEPH) reference families) and on the telomeric side by F13A at a recombination fraction of 0.19. See, L. P. W. Ranum et al., *Am. J. Hum. Genet.*, 49, 31–41 (1991). Both of these markers are quite distant and are not practical for use in efforts aimed at cloning the SCA1 gene. The D6S89 marker maps closer to the SCA1 gene.

To localize SCA1 more precisely, five dinucleotide polymorphisms near D6S89 have been identified. A new marker, AM10GA, demonstrates no recombination with SCA1. Linkage analysis and analysis of recombination events confirm that SCA1 maps centromeric to D6S89 with D6S109 as the other flanking marker at the centronomic end and establishes the following order: CEN-D6S109-AM10GA/SCA1-D6S89-LR40-D6S202-TEL. The genetic distance between the two flanking markers, D6S109 and D6S89, is about 6.7 cM based on linkage analysis using 40 reference families from the Centre d'Etude du Polymorphisme Humain (CEPH).

The size of the SCA1 candidate region of the short arm of chromosome 6 containing the SCA1 locus is about 1.2 Mb. The SCA1 locus is located within a 3.36-kb EcoRI fragment, and contains a highly polymorphic CAG repeat. This region of CAG repeating sequences is unstable and expanded in individuals with SCA1. Southern and PCR analyses of the $(CAG)_n$ repeat demonstrate a direct correlation between the size of the repeat expansion and the age-at-onset of SCA1, with larger alleles occurring in juvenile cases. These results demonstrate that SCA1, like fragile X syndrome, myotonic dystrophy, X-linked spinobulbar muscular atrophy, and Huntington disease, displays a mutational mechanism involving expansion of an unstable trinucleotide repeat.

The identification of a trinucleotide repeat expansion associated with SCA1 allows for improved diagnosis of the disease. Thus, the present invention also relates to methods of diagnosing SCA1. These diagnostic methods can involve any known method for detecting a specific fragment of DNA. For example, hybridization techniques using labelled probes can be used. Alternatively, PCR techniques can be used with novel primers that amplify the CAG repeating region of the EcoRI fragment.

DNA probes can be used for identifying DNA segments of the affected allele of the SCA1 gene. DNA probes are segments of labelled, single-stranded DNA which will hybridize, or noncovalently bind, with complementary single-stranded DNA derived from the gene sought to be identified. The probe can be labelled with any suitable label known to those skilled in the art, including radioactive and nonradioactive labels. Typical radioactive labels include $^{32}P$, $^{125}I$, $^{35}S$, and the like. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. The probe may also be labelled at both ends with different types of labels for ease of separation, as, for example, by using an isotopic label at one end and a biotin label at the other end.

Using DNA probe analysis, the target DNA can be derived by the enzymatic digestion, fractionation, and denaturation of genomic DNA to yield a complex mixture incorporating the DNA from many different genes, including DNA from the short arm of chromosome 6, which includes the SCA1 locus. A specific DNA gene probe will hybridize only with DNA derived from its target gene or gene fragment, and the resultant complex can be isolated and identified by techniques known in the art.

In general, for detecting the presence of a DNA sequence located within an SCA1 gene, the genomic DNA is digested with a restriction endonuclease to obtain DNA fragments. The source of genomic DNA to be tested can be any medical specimen that contains DNA. Examples include specimen of blood, semen, vaginal swabs, tissue, hair, and body fluids. The restriction endonuclease can be any that will cut the genomic DNA into fragments of double-stranded DNA having a particular nucleotide sequence. The specificities of numerous endonucleases are well known and can be found in a variety of publications, e.g. Molecular Cloning: A Laboratory Manual by Maniatis et al., Cold Spring Harbor Laboratory 1982. That manual is incorporated herein by reference in its entirety. Preferred restriction endonuclease enzymes include EcoRI, TaqI, and BstNI. EcoRI is particularly preferred.

Diagnosis of the disease can alternatively involve the use of the polymerase chain reaction sequence amplification method (PCR) using novel primers. U.S. Pat. No. 4,683,195 (Mullis et al., issued Jul. 28, 1987) describes a process for amplifying, detecting and/or cloning nucleic acid sequences. The method involves treating extracted DNA to form single-stranded complementary strands, treating the separate complementary strands of DNA with two oligonucleotide primers, extending the primers to form complementary extension products that act as templates for synthesizing the desired nucleic acid sequence; and detecting the amplified sequence. More specifically, the method steps of treating the DNA with primers and extending the primers include the steps of: adding a pair of oligonucleotide primers, wherein one primer of the pair is substantially complementary to part of the sequence in the sense strand and the other primer of each pair is substantially complementary to a different part of the same sequence in the complementary antisense strand; annealing the paired primers to the complementary sequence; simultaneously extending the annealed primers from a 3' terminus of each primer to synthesize an extension product complementary to the strands annealed to each primer wherein said extension products after separation from the complement serve as templates for the synthesis of an extension product for the other primer of each pair; and separating said extension products from said templates to produce single-stranded molecules. Variations of the method are described in U.S. Pat. No. 4,683,194 (Saiki et al., issued Jul. 28, 1987). The polymerase chain reaction sequence amplification method is also described by Saiki et. al., *Science*, 230, 1350–1354 (1985) and Scharf et. al., *Science*, 233, 1076–1078 (1986). The discussion of the these techniques in each of these references is incorporated herein by reference.

The primers are oligonucleotides, either synthetic or naturally occurring, capable of acting as a point of initiating synthesis of a product complementary to the region of the DNA sequence containing the CAG repeating trinucleotides of the SCA1 locus of the EcoRI fragment of the short arm of chromosome 6. The primer includes a nucleotide sequence substantially complementary to a portion of a strand of an affected or a normal allele of a 3.36 kb EcoRI fragment of an SCA1 gene having a $(CAG)_n$ region. The primer sequence has at least about 11 nucleotides, preferably at least about 16 nucleotides and no more than about 35 nucleotides. The primers are chosen such that they produce a primed product of about 70–350 base pairs, preferably about 100–300 base pairs. More preferably, the primers are chosen such that nucleotide sequence is substantially complementary to a portion of a strand of an affected or a normal allele within about 150 nucleotides on either side of the $(CAG)_n$ region, including directly adjacent to the $(CAG)_n$ region.

Examples of preferred primers are shown by solid lines with arrowheads in FIG. 3. The primers are thus selected from the group consisting of CCGGAGCCCTGCTGAGGT (CAG-a) (SEQ ID NO:8), CCAGACGCCGGGACAC (CAG-b) (SEQ ID NO:9), AACTGGAAATGTGGACG-TAC (Rep-1) (SEQ ID NO:10), CAACATGGGCAGTCT-GAG (Rep-2) (SEQ ID NO:11), CCACCACTCCATC-CCAGC (GCT-435) (SEQ ID NO:12), TGCTGGGCTGGTGGGGGG (GCT-214) (SEQ ID NO:13), CTCTCGGCTTTCTTGGTG (Pre-1) (SEQ ID NO:14), and GTACGTCCACATTTCCAGTT (Pre-2) (SEQ ID NO:15). These primers can be used in various combinations or with any other primer that can be designed to hybridize to a portion of DNA of a 3.36 kb EcoRI fragment of an SCA1 gene having a CAG repeat region. For example, the primer labelled Rep-2 can be combined with the primer labelled CAG-a, and the primer labelled CAG-b can be combined with the primer labelled Rep-1. More preferably the primers are the sets of primer pairs designed as CAG-a/CAG-b, Rep-1/Rep-2, Rep-1/GCT-435, for example. These primer sets successfully amplify the CAG repeat units of interest using PCR technology. Alternatively, they can be used in various known techniques to sequence the SCA1 gene.

Other methods of diagnosis can be used as well. These include, for example, using a variety of electrophoresis techniques to detect slight changes in the nucleotide sequence of the 3.36-kb EcoRI fragment of the SCA1 gene. Further nonlimiting examples include denaturing gradient electrophoresis, single strand conformational polymorphism gels, and nondenaturing gel electrophoresis techniques.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

Thus, the present invention can be used in family counseling, planning medical treatment, and in standard work-ups of patients with ataxia of unknown etiology.

Experimental Section

I. The Gene for SCA1 Maps Centromeric to D6S89

To confirm the position of SCA1 with respect to D6S89 and to identify closer flanking markers, two dinucleotide repeat polymorphisms D6S109 and D6S202 were used. Using YAC clones isolated in the D6S89 region, three additional dinucleotide repeat polymorphisms were identified, one of which (AM10GA) showed no recombination with SCA1 and confirmed that D6S89 is telomeric to SCA1. The dinucleotide repeat at D6S109 revealed six recombination events with SCA1 and determined D6S109 to be the other flanking marker at the centromeric end. Linkage analysis, physical mapping data as discussed below, and analysis of recombination events demonstrated that the order of markers is as follows: CEN-D6S109-AM10GA/SCA1-D6S89-SB1-LR40-D6S202-TEL.

A. Materials and Methods

1. SCA1 Kindreds

Nine large SCA1 families were used in the present study. Clinical findings and linkage data demonstrating that these families segregated SCA1 have been previously reported. See, J. F. Jackson et. al., *N. Engl. J. Med.*, 296, 1138–1141 (1977); B. J. B. Keats et al., *Am. J. Hum. Genet.*, 49, 972–977 (1991); L. P. W. Ranum et. al., *Am. J. Hum. Genet.*, 49, 31–41 (1991); and H. Y. Zoghbi et al., *Am. J. Hum. Genet.*, 49, 23–30 (1991). Analysis of polymorphisms at the loci D6S109, AM10GA, SB1, LR40, and D6S202 was performed on individuals from these kindreds.

The Houston (TX-SCA1) kindred included 106 individuals, of whom 57 (25 affected) were genotyped. See, H. Y. Zoghbi et al., *Ann. Neurol.*, 23, 580–584 (1988). Patients symptomatic at the time of exam, as well as asymptomatic individuals who had both a symptomatic child and a symptomatic parent, were classified as "affected". In this kindred, a deceased individual previously assigned as affected (from family history data) was reassigned an unknown status after review of medical records. This reassignment eliminated what was previously thought to be a recombination event between SCA1 and D6S89 in the TX-SCA1 kindred. To maximize the amount of information available for linkage analysis, the two chromosomes 6 in somatic cell hybrids for 15 affected individuals and one unaffected individual from the TX-SCA1 kindred were separated. See, H. Y. Zoghbi et al., *Am. J. Hum. Genet.*, 44, 255–263 (1989). The Louisiana (LA-SCA1) kindred included 50 individuals of whom 26 (8 affected) were genotyped. See, B. J. B. Keats et al., *Am. J. Hum. Genet.*, 49, 972–977 (1991). The Minnesota (MN-SCA1) kindred included 175 individuals, of whom 106 (17 affected) were genotyped. See, J. L. Haines et al., *Neurology*, 34, 1542–1548 (1984); and L. P. W. Ranum et al., *Am. J. Hum. Genet.*, 49, 31–41 (1991). The Michigan (MI-SCA1) kindred included 201 individuals, of whom 127 (25 affected)

were genotyped. See, H. E. Nino et al., *Neurology*, 30, 12–20 (1980). The Mississippi (MS-SCA1) kindred included 84 individuals, of whom 37 (17 affected) were genotyped. See, J. F. Jackson et al., *N. Engl. J. Med.*, 296, 1138–1141 (1977).

Four Italian families segregating SCA1 were analyzed; their clinical phenotype and HLA linkage data were reported previously. See, M. Spadaro et al., *Acta Neurol. Scand.*, 85, 257–265 (1992). Three families originated in the Calabria Region (Southern Italy): family IT-P with 135 members of whom 80 (21 affected) were genotyped; for computational reasons, the family was subdivided into 3 different pedigrees (RM, VI, and FB) and only one of the 3 consanguinity loops was considered; family IT-NS, with 43 members of whom 27 (7 affected) were typed; family IT-NS with 51 members of whom 16 (3 affected) were typed. The fourth family, IT-MR, originated from Latium and consisted of 17 individuals of whom 10 (4 affected) were genotyped.

2. CEPH Families

The 40 CEPH reference families were genotyped at the D9S109, LR40 and D6S202 loci in order to provide a large number of informative meioses for marker-marker linkage analyses. Markers AM10GA and SB1 flank D6S89, having been isolated from a yeast artificial chromosome (YAC) contig built bidirectionally from D6S89 (see below). A subset of 18CEPH families which defined 26 recombinants between D6S109 and D6S89 was genotyped at AM10GA and SB1 in order to determine the order of AM10GA, D6S89 and SB1 with respect to D6S109.

3. Cloning of Sequences Containing Dinucleotide Repeats

The identification and description of polymorphic dinucleotide repeats at the D6S109 and D6S202 loci have been previously reported. See, L. P. W. Ranum et al., *Nucleic Acids Res.*, 19, 1171 (1991); and F. LeBorgne-Demarquoy et. al., *Nucleic Acids Res.*, 19, 6060 (1991).

DNA fragments containing dinucleotide repeats were cloned at LR40 and SB1 from yeast artificial chromosome (YAC) clones at the LR40 and FLB1 loci, respectively (see below). DNA from each YAC clone was amplified in a 50 µl reaction containing 20 ng DNA, a single Alu primer (see below), 50 mM KCl, 10 mM Tris-Cl pH 8.3, 1.25 mM MgCl$_2$, 200 or 250 µM dNTPs, 0.01% (w/v) gelatin, and 1.25 units Thermus aquaticus DNA polymerase (Taq polymerase-Perkin Elmer-Cetus, Norwalk, Conn.). For amplification of FLB1 YAC DNA, a primer complementary to the 5' end of the Alu consensus sequence (Oncor Laboratories), designated SAL1, was used=5'-AGGAGTGAGCCACCGCACCCAGCC-3' (SEQ ID NO:16) at a final concentration of 0.6 µM. For amplification of LR40 YAC DNA, 0.2 µM primer PDJ34 was used. See, C. Breukel et al., *Nucleic Acids Res.*, 18, 3097 (1990). Samples were overlaid with mineral oil, denatured at 94° C. for 5 min., then subjected to 30 cycles of 1 min. 94° C. denaturation, 1 min. 55° C. annealing, and 5 min. 72° C. extension. The last extension step was lengthened to 10 min. Electrophoresis of 15 µl of PCR products was performed on a 1.5% agarose gel, which was Southern blotted and hybridized with a probe prepared by random-hexamer-primed labelling of synthetic poly(dG-dT)-poly(dA-dC) (Pharmacia, Piscataway, N.J.) using [α-$^{32}$P]dCTP, as described by A. P. Feinberg et al., *Anal. Biochem.*, 137. 266–267 (1984). Fragments hybridizing with the dinucleotide repeat probe were identified and were subsequently purified by electrophoresis on a low-melt agarose gel. Fragments were excised and reamplified by PCR as above.

For LR40, reamplified DNA was repurified by low-melt gel electrophoresis, and DNA extracted from excised bands by passage through a glasswool spin column as described by D. M. Heery et al., *Trends Genet.*, 6, 173 (1990). A purified 1.2-kb fragment was cloned into pBluescript plasmid modified as a "T-vector" as described by D. Marchuck et al., *Nucleic Acids Res.*, 19, 1154 (1990). From this clone, a 0.6-kb HincII restriction fragment containing a GT repeat was subcloned into pBluescript plasmid, and sequenced on an Applied Biosystems, Inc. (Foster City, Calif.) automated sequencer.

For SB1, a reamplified 1-kb fragment was ethanol precipitated and blunt-end cloned into pBluescript plasmid. Plasmid DNA was isolated and PCR amplified in one reaction with M13 Reverse primer plus BamGT primer (5'-CCCGGATCCTGTGTGTGTGTGTGTGTG-3') (SEQ ID NO:17) and in a second reaction M13 Universal primer and BamCA primer (5'-CCCGGATCCACACACACACACACACAC-3') (SEQ ID NO:18). See, C. A. Feener et al., *Am. J. Hum. Genet.*, 48, 621–627 (1991). PCR conditions were as above except primers were used at 1 µM concentration; 2.5 units Taq polymerase and approximately 30 ng DNA were used per reaction, with final reaction volumes of 100 µl, and an annealing temperature of 50° C.). Products were precipitated, resuspended, and digested with BamH1 (product of Universal primer reaction) or BamH1 and HincII (product of Reverse primer reaction). These two fragments were cloned into pBluescript plasmid and sequenced as above.

Dinucleotide repeats were cloned at AM10 from a YAC containing this locus. A λFixII library was constructed using DNA from this yeast clone, and human clones were identified by filter hybridization using human placental DNA as a probe. A gridded array of these human clones was grown, and filters containing DNA from these clones were hybridized with a $^{32}$P-labelled poly(dG-dT)-poly(dA-dC3) probe as described above. DNA was prepared from positive clones, digested with various restriction enzymes, and analyzed by agarose gel electrophoresis. Southern blotting and hybridization were carried out with the poly(dG-dT)-poly(dA-dC) probe. A 1-kb fragment hybridizing with the dinucleotide repeat probe was identified, cloned into M13, and sequenced.

4. PCR Analysis

Primer sequences and concentrations, and PCR cycle times used for amplification of dinucleotide repeat sequences from human genomic DNA are presented in Table 1. For the LR40 polymorphism, primer set "A" was used for analysis of the TX-SCA1, LA-SCA1, and MS-SCA1 kindreds, while palmer set "B" was used for all other kindreds. Buffer compositions were as follows: 50 mM KCl, 10 mM Tris-Cl pH 8.3, 1.25 mM MgCl$_2$ (1.5 mM MgCl$_2$ for AM10GA), 250 µM dNTPs (200 µM dNTPs for AM10GA), 0.01% (w/v) gelatin, and 0.5–0.625 unit Taq polymerase. For the LR40 analysis, 2% formamide was included in the PCR buffer. When primer set B was used for LR40 analysis, 125 µM dNTPs, 1.5 mM MgCl$_2$, and 1 unit Taq polymerase were used. All reaction volumes were 25 µl and contained 40 ng genomic DNA. Four microliters of each reaction was mixed with 2 µl formamide loading buffer, denatured at 90°–100° C. for 3 min., cooled on ice, and 2–4 µl was used for electrophoresis on a 4% or 6% polyacrylamide/7.65M urea sequencing gel for 2–3 hours at 1100 V. PCR assay conditions have been reported previously for D6S202 and D6S109. See, L. P. W. Ranum et al., *Nucleic Acids Res.*, 19, 1171 (1991); and F. LeBorgne-Demarquoy et al., *Nucleic Acids Res.*, 19, 6060 (1991).

TABLE 1

Primers and PCR conditions for amplification of dinucleotide repeat sequences

| Mark/Type | Primers[a] | PCR Steps | Cycles |
|---|---|---|---|
| AM10GA/(GA)$_n$ | AAGTCAGCCTCTACTCTTTGTTGA (SEQ ID NO:19) CTTGGAGCAGTCTGTAGGGAG (SEQ ID NO:20) | 94° C. for 30 sec. 52 C. for 30 sec. 72° C. for 30 sec. | 30 |
| SB1/(GT)$_n$ | TGAAGTGATGTGCTCTGTTC (SEQ ID NO:21) AAAGGGGTAGAGGAAATGAG (SEQ ID NO:22) | 94° C. for 60 sec. 60° C. for 60 sec. 72° C. for 60 sec. | 30 |
| LR40/(GT)$_N$ set A | AGGAGAGGGGTCATGAGTTG (SEQ ID NO:23) GGCTCATGAATACATTACATGAAG (SEQ ID NO:24) | 94° C. for 60 sec. 58° C. for 60 sec. 72° C. for 60 sec. | 25 |
| LR40/(GT)$_n$ set B | CTCATTCACCTTAGAGACAAATGGATAG (SEQ ID NO:25) ATGGTATAGGGATTTTNCCAAACCTG (SEQ ID NO:26) | 94° C. for 60 sec. 60° C. for 60 sec. 72° C. for 45 sec. | 27 |

[a]Primers are shown as 5' to 3' sequence. The first primer of each pair was end-labelled with $\gamma$-$^{32}$P ATP and polynucleotide kinase. Primer concentrations were 1 μM.

5. SCA1 Linkage Analysis

The D6S109, AM10GA, D6S89, SB1, LR40 and D6S202 markers were analyzed for linkage to SCA1 using the computer program LINKAGE version 5.1 which includes the MLINK, ILINK, LINKMAP, CLODSCORE and CMAP programs. See, G. M. Lathrop et. al., *Proc. Natl. Acad. Sci. USA*, 81, 3443–3446 (1984). Age dependent penetrance classes were assigned independently for each of the families included in the analysis. Marker allels were recoded to reduce the number of alleles segregating in a family to four, five or six alleles to simplify the analysis. The allele frequencies for the various markers were based on the frequencies of the alleles among the spouses in each family and were determined separately for the two American black kindreds, for the Italian kindreds, and for the Caucasian kindreds from Minnesota, Michigan, and Mississippi, with the following exception—the allele frequencies for D6S109 in the MI and MN kindreds were based on the frequencies of the alleles in the CEPH families.

Maximum LOD scores for the various markers were calculated with the MLINK program by running each of the analyses separately for the various families, at theta values with increments of 0.0005 to 0.001, and then adding the values of each of the kindreds. The analyses were done separately to ensure that the allele frequencies for the various markers were representative for each of the ethnically diverse families. As a control, the recombination fractions at the maximum lod scores ($Z_{max}$) between each marker and SCA1 were calculated using the ILINK program after the allele frequencies for each marker were set equal to one another. In all cases the recombination frequencies were the same and $Z_{max}$ values were very similar to those reported in Table 5 below.

6. CEPH Linkage Analysis

Forty CEPH families were typed for the GT repeat markers D6S109, D6S202 and LR40. The original alleles were recoded to five alleles. The SB1 and AM10 markers were typed in a subset of the CEPH panel which defined 26 recombinants from 18 different families between D6S109 and D6S89. The CLODSCORE program was used for the two-point analyses and CMAP was used for the three-and four-point analyses. For the three-point and four-point analyses, the interval between the mapped markers was fixed based on the two point $\theta_m=\theta_f$ results. The likelihood of the location of the test locus (SCA1) was calculated at 10 different positions within each interval. The test for sex difference in the Θ values was performed using a $\chi^2$ statistic, with $\chi^2=2(\ln 10)[Z(\theta_m,\theta_f) -Z(\theta=0_m=\theta_f)]$, where $Z(\theta_m, \theta_f)$ is the overall $Z_{max}$ for arbitrary $\theta_m$ and $\theta_f$, while $Z(\theta=\theta_m=\theta_f)$ is the $Z_{max}$ constrained to $\theta_m=\theta_f$. Under homogeneity (H1), $\chi^2$ approximates a $\chi^2$ with 1 d.f. Rejection of homogeneity occurs when $\chi^2>3.84$.

B. Results

1. Dinucleotide Repeat Cloning and Sequencing and Analysis

Dinucleotide repeats SB1 and LR40 were amplified directly from YAC clones by Alu-primed PCR and the dinucleotide repeat containing fragments were identified by hybridization. The PCR products were cloned either directly or by further amplification using tailed poly(GT) or poly(CA) primers paired with an Alu primer. In addition, two dinucleotide repeats were subcloned from a lambda phage clone from a library constructed from a YAC at the AM10 locus.

Dinucleotide repeats from the SB1, LR40, and AM10 loci were sequenced. At LR40, the cloned repeat sequence was (CA)$_{16}$TA(CA)$_{10}$ (SEQ ID NO:27). The AM10 fragment contained two repeat sequences separated by 45 bp of nonrepeat sequence. The first repeat, designated AM10GA, was (GA)$_2$ATGACA(GA)$_{11}$ (SEQ ID NO:28). The second repeat, designated AM10GT, was not used in this study because upon analysis of the TX-SCA1 kindred it yielded the same information as the AM10GA repeat. The AM10GT repeat consists of (GA)$_2$AA(GA)$_6$GTGA(GT)$_{16}$AT(GT)$_5$ (SEQ ID NO:29). Primer information for AM10GT is available through the Genome Data Base. At SB1, the repeat tract was not sequenced; only flanking sequence was determined.

As there are differences in allele distributions of markers among the different races, allele frequencies are reported here separately for the CEPH kindreds (Caucasian) and the TX-SCA1 kindred (American black) (Table 2). CEPH allele frequencies were based on 72 independent chromosomes for SB1, 82 independent chromosomes for AM10, and on the full set of 40 families for D6S109 and LR40. TX-SCA1 allele frequencies were based on 45 independent chromosomes for LR40, 43 independent chromosomes for SB1, 45 independent chromosomes for AM10, and 42 independent chromosomes for D6S109.

TABLE 2

Allele frequencies of new markers

| Allele[a] | $D_6S109$[b] TXSCA₁ | AM₁₀GA TXSCA₁ | AM₁₀GA CEPH | SB₁ TXSCA₁ | SB₁ CEPH | LR₄₀ TXSCA₁ | LR₄₀ CEPH | $D_6S202$[b] TXSCA1 |
|---|---|---|---|---|---|---|---|---|
| A₀ | — | — | 0.012 | 0.070 | — | — | — | — |
| A₁ | 0.048 | 0.022 | 0.024 | 0.163 | 0.027 | 0.244 | 0.022 | 0.05 |
| A₂ | 0.024 | 0.289 | 0.220 | 0.186 | 0.166 | 0.045 | 0.043 | 0.11 |
| A₃ | 0.119 | — | 0.024 | 0.070 | 0.333 | 0.111 | 0.065 | 0.11 |
| A₄ | 0.024 | 0.333 | 0.232 | 0.023 | — | 0.133 | 0.033 | 0.13 |
| A₅ | 0.071 | 0.267 | 0.488 | 0.186 | 0.097 | 0.111 | 0.272 | 0.11 |
| A₆ | 0.261 | — | — | 0.093 | 0.111 | — | 0.098 | 0.03 |
| A₇ | 0.024 | 0.089 | — | 0.093 | 0.153 | 0.022 | 0.054 | 0.22 |
| A₈ | 0.095 | — | — | 0.093 | 0.083 | 0.045 | 0.076 | 0.13 |
| A₉ | 0.143 | — | — | — | 0.014 | 0.089 | 0.054 | 0.08 |
| A₁₀ | — | — | — | — | — | 0.022 | 0.065 | 0.03 |
| A₁₁ | 0.048 | — | — | 0.023 | — | 0.133 | 0.011 | — |
| A₁₂ | 0.048 | — | — | — | — | 0.045 | 0.054 | — |
| A₁₃ | 0.048 | — | — | — | 0.014 | — | 0.097 | — |
| A₁₄ | 0.071 | — | — | — | — | — | 0.033 | — |
| A₁₅ | — | — | — | — | — | — | 0.023 | — |

[1]Alleles are numbered such that the largest allele is assigned the lowest number and each successive allele is two bp smaller. For $D_6S_{109}$, $A_1$ = 215 bp, for $Am_{10}GA$, $A_0$ = 123 bp, for B1, $A_0$ = 220 bp, for $LR_{40}$, $A_1$ = 241 bp, (primer set A, Table 1), CEPH $A_1$ = 267 bp (primer set B, Table 1), for $D_6S_{202}$, $A_1'$ = 154 bp.
[b]CEPH data published for $D_{6109}$ (Ranum et al. Nucleic Acids Res., 19, 1171 (1991) and $D_6S_{202}$ (LeBorgne-Demarquoy et al., Nucleic Acids Res., 19, 6060 1991).

2. Genetic Linkage Data a. CEPH families. In order to establish a well-defined genetic map for the SCA1 region, newly isolated DNA markers were mapped using the CEPH reference families. Results of pairwise linkage analyses in CEPH kindreds are shown in Table 3. No recombination was observed between AM10GA and D6S89 ($\theta$=0.00, $Z_{max}$=15.1) using a subset of the CEPH panel which defined 26 recombinants between D6S109 and D6S89. The markers D6S109 and LR40 are close to D6S89, with recombination fractions of 0.067 ($Z_{max}$=71.4) and 0.04 ($Z_{max}$=84.5) respectively.

Selected multipoint analyses were performed to position the newly isolated markers D6S109, LR40, D6S202 with respect to markers previously mapped using the CEPH panel. The CMAP program was used for three- and four-point linkage analyses to position D6S109 relative to D6S88 and D6S89 and to position LR40 and D6S202 relative to each other and to D6S89 and F13A. For the three-point analyses, the D6S88-D6S89 interval was fixed based on the two-point recombination fraction in CEPH and the lod score was calculated at various recombination fractions. The order D6S88-D6S109-D6S89 is favored over the next most likely order by odds of 4×10³: 1 (Table 4). For the four-point analyses, both the D6S89-D6S202-F13A and the D6S89-LR40-F13A intervals were fixed based on the two-point recombination fractions; lod scores were then calculated for LR40 and D6S202 at various $\theta$ values on the respective fixed maps. The order D6S89-LR40-D6S202-F13A is favored over the next most likely order in both analyses; odds in favor were 400 to 1 when the position of LR40 was varied and were 1×10⁶ to 1 when D6S202 was varied (Table 4).

The order of AM10GA and D6S89 could not be determined using the D6S109/D6S89 CEPH recombinants. However, the order AM10GA -D6S89-SB1 was deduced by characterization of overlapping yeast artificial chromosome clones containing these markers (see below). Furthermore, one end of this contig is present in a well characterized radiation-reduced hybrid known to contain D6S109 and other centromeric markers, indicating the order D6S109-AM10GA -D6S89-SB1.

TABLE 3

Pairwise linkage results in CEPH

| Marker Pair | $\Theta_m = \Theta_f$ | $Z_{max}$ | $\Theta_m$ | $\Theta_f$ | $Z_{max}$ | $\chi^2$ |
|---|---|---|---|---|---|---|
| HLA and | 0.128 | 26.4 | 0.103 | 0.168 | 26.8 | 1.86 |
| D6S88 | | | | | | |
| D6S109 | 0.126 | 48.4 | 0.062 | 0.176 | 51.0 | 12.1* |
| AM10 | 0.608 | 0.0440 | 0.301 | 0.500 | 0.246 | 0.929 |
| D6S89 | 0.158 | 43.3 | 0.091 | 0.225 | 46.6 | 15.2* |
| SB1 | 0.574 | 0.0190 | 0.299 | 0.500 | 0.400 | 0.381 |
| LR40 | 0.213 | 25.5 | 0.116 | 0.306 | 30.0 | 20.8* |
| HZ30 | 0.251 | 21.6 | 0.191 | 0.318 | 23.6 | 8.95* |
| F13A | 0.291 | 8.81 | 0.255 | 0.326 | 9.14 | 1.52 |
| D6S88 and | 0.017 | 48.6 | 0.024 | 0.009 | 48.8 | 0.846 |
| D6S109 | | | | | | |
| AM10 | 0.654 | 0.0290 | 0.499 | 0.696 | 0.047 | 0.0820 |
| D6S89 | 0.086 | 36.1 | 0.076 | 0.098 | 36.2 | 0.0750 |
| SB1 | 0.203 | 1.09 | 0.136 | 0.687 | 1.36 | 1.27 |
| LR40 | 0.088 | 31.1 | 0.078 | 0.104 | 31.2 | 0.350 |
| HZ30 | 0.135 | 30.4 | 0.124 | 0.152 | 30.4 | 0.340 |
| F13A | 0.180 | 10.2 | 0.158 | 0.217 | 10.3 | 0.626 |
| D6S109 and | 0.730 | 0.933 | 0.170 | 0.502 | 1.67 | 3.39 |
| AM10 | | | | | | |
| D6S89 | 0.067 | 71.4 | 0.035 | 0.090 | 72.5 | 5.15* |
| SB1 | 0.742 | 1.95 | 0.113 | 0.501 | 4.32 | 10.9* |
| LR40 | 0.109 | 50.6 | 0.050 | 0.152 | 52.9 | 10.5* |
| HZ30 | 0.162 | 36.6 | 0.147 | 0.174 | 36.7 | 0.515 |
| F13A | 0.207 | 14.4 | 0.211 | 0.204 | 14.4 | 0.0368 |
| AM10 and | 0.000 | 15.1 | 0.000 | 0.000 | 15.1 | 0.000 |
| D6S89 | | | | | | |
| SB1 | 0.000 | 13.2 | 0.000 | 0.000 | 13.2 | 0.000 |
| LR40 | 0.021 | 8.74 | 0.000 | 0.050 | 9.11 | 1.74 |
| HZ30 | 0.000 | 13.8 | 0.000 | 0.000 | 13.8 | 0.000 |
| F13A | 0.135 | 3.48 | 0.042 | 0.253 | 4.39 | 4.16* |
| D6S89 and | 0.000 | 25.0 | 0.000 | 0.000 | 25.0 | 0.000 |
| SB1 | | | | | | |
| LR40 | 0.040 | 84.5 | 0.030 | 0.049 | 84.7 | 0.925 |
| HZ30 | 0.078 | 76.0 | 0.075 | 0.077 | 76.0 | 0.0230 |
| F13A | 0.151 | 30.7 | 0.139 | 0.160 | 30.7 | 0.248 |
| SB1 and | 0.033 | 14.4 | 0.022 | 0.044 | 14.5 | 0.350 |
| LR40 | | | | | | |
| HZ30 | 0.026 | 17.5 | 0.032 | 0.020 | 17.5 | 0.0300 |
| F13A | 0.136 | 4.80 | 0.119 | 0.155 | 4.84 | 0.170 |
| LR40 and | 0.079 | 64.8 | 0.092 | 0.050 | 65.0 | 1.09 |

TABLE 3-continued

Pairwise linkage results in CEPH

| Marker Pair | $\Theta_m = \Theta_f$ | $Z_{max}$ | $\Theta_m$ | $\Theta_f$ | $Z_{max}$ | $\chi^2$ |
|---|---|---|---|---|---|---|
| HZ30 F13A | 0.131 | 29.1 | 0.121 | 0.140 | 29.2 | 0.189 |
| HZ30 and F13A | 0.109 | 38.4 | 0.122 | 0.106 | 38.4 | 0.0092 |

*Indicates statistically significant differences were observed in the recombination fractions when the assumption of homogeneity ($\Theta_m = \Theta_f$) was rejected; that is the likelihood that $\chi^2 > 3.84$ with 1 df should occur by chance in P < 0.05.

TABLE 4

Three and four point linkage analyses in the CEPH families

| Order | Z max | Relative Odds | Odds in favor |
|---|---|---|---|
| D6S109-D6S88-D6S89 | 90.6 | $2 \times 10^1$ | |
| D6S88-D6S109-D6S89 | 94.2 | $8 \times 10^{11}$ | $4 \times 10^3$ |
| D6S88-D6S89-D6S109 | 82.3 | 1 | |
| LR40-D6S89-D6S202-F13A | 96.1 | $1 \times 10^{34}$ | |
| D6S89-LR40-D6S202-F13A | 98.6 | $4 \times 10^{36}$ | 400:1 |
| D6S89-D6S202-Lr40-F13A | 73.9 | $8 \times 10^{11}$ | |
| D6S89-D6S202-F13A-LR40 | 62.0 | 1 | |
| D6S202-D6S89-LR40-F13A | 89.5 | $1 \times 10^{32}$ | |
| D6S89-D6S202-LR40-F13A | 57.5 | 1 | |
| D6S89-LR40-D6S202-F13A | 95.5 | $1 \times 10^{38}$ | $10^6:1$ |
| D6S89-LR40-F13A-D6S202 | 77.6 | $1 \times 10^{20}$ | | b. SCA1 kindreds. Results of pairwise linkage analyses in SCA1 kindreds are shown in Table 5. AM10GA, D6S89, and SB1 are all closely linked to SCA1. No recombination was observed between AM10GA and SCA1; the lod score is 42.1 at a recombination fraction of 0.00. The recombination fraction between D6S89 and SCA1 is 0.004 (lod score of 67.6). The recombination fraction between SB1 and SCA1 is 0.007 (lod score of 39.5). D6S109, LR40 and D6S202 are linked to SCA1 as well, but at greater distances (recombination fractions of 0.04, 0.03, and 0.08 respectively). Based on genetic mapping in nine large kindreds, the SCA1 locus is very close to D6S89 and AM10GA, with a $Z_{max}-1$ support interval less than or equal to 0.02 in both cases.

3. Analysis of Key Recombinants

One recombination event between D6S89 and SCA1 has been confirmed in an affected individual. The patient, individual MI-2 in FIG. 4, was also recombinant at SB1, although uninformative at LR40 and D6S202. He carried a disease haplotype at the HLA, D6S109 and AM10 loci, demonstrating that SCA1 is centromeric to D6S89, as indicated by the rightmost arrow in FIG. 4. To eliminate the possibility of sample mix-up, the patient's DNA was reextracted from a hair sample and retyped for D6S109, D6S89, D6S202, LR40, AM10GA, and SB1. The results from the hair sample matched those from the cell line originally established from the patient's blood. The patient's medical records were carefully reexamined and it was confirmed that he did indeed have ataxia. In addition, his haplotypes were consistent with those of a sister and a daughter.

D6S109 lies centromeric to D6S89; six recombination events have been observed between D6S109 and SCA1, as shown in FIG. 4. At this point, D6S109 is the centromeric marker closest to SCA1. The arrows in FIG. 4 denote the maximum region common to all affected chromosomes, and therefore the maximum possible region containing the SCA1 gene, which extends from D6S89 to D6S109.

No additional marker-SCA1 recombination events have been observed between D6S89 and SB1. Markers further telomeric to SB1 show additional recombination with SCA1—one recombination event between SCA1 and LR40 and three recombination events between SCA1 and D6S202. These events are depicted in FIG. 4 (all recombination events depicted in FIG. 4 are in affected individuals).

II. Mapping and Cloning the Critical Region of the SCA1 Gene

A. Materials and Methods

1. Cell lines

I-7 is a human-hamster hybrid cell line which contains the short arm of chromosome 6 as its only human chromosome. See, H. Y. Zoghbi et al., Genomics, 6, 352–357 (1990). R86, R78, R72, R54 and R17 are radiation reduced hybrid cell lines retaining various portions of 6p22-23. See, H. Y. Zoghbi et al., Genomics, 9, 713–720 (1991).

2. Generation of new DNA markers and STSs

DNA from a radiation reduced hybrid retaining D6S89 (R86) and DNAs from four radiation hybrids (R78, R72, R54 and R17) which do not retain D6S89 but retain markers immediately flanking D6S89 were used in comparative Alu-PCR to isolate region-specific DNA markers. See, D. L. Nelson et al., Proc. Natl. Acad. Sci. USA, 86, 6686–6690 (1989); and H. Y. Zoghbi et al., Genomics, 9, 713–720 (1991). Alu-PCR was carded out using Alu primers 559 and 517 individually (D. L. Nelson et. al., Proc. Natl. Acad. Sci.

TABLE 5

Pairwise lod scores for SCA1 and dinucleotide repeat markers

| | Recombination fraction | | | | | | | | | Support |
|---|---|---|---|---|---|---|---|---|---|---|
| | 0 | 0.001 | 0.05 | 0.1 | 0.2 | 0.3 | 0.4 | $Z^a$ | $\Theta^a$ | Interval[b] |
| SCA1:d6S109 | $-\infty$ | 22.68 | 33.81 | 32.03 | 25.19 | 16.56 | 7.24 | 33.82 | 0.04 | 0.02 to 0.09 |
| SCA1:AM10GA | 42.14 | 42.06 | 38.48 | 34.51 | 25.86 | 16.63 | 7.30 | 42.14 | 0.00 | 0.00 to 0.02 |
| SCA1:D6S89 | $-\infty$ | 67.35 | 62.78 | 56.39 | 42.51 | 27.56 | 12.09 | 67.58 | 0.004 | 0.00 to 0.002 |
| SCA1:SB | $-\infty$ | 39.02 | 37.33 | 33.92 | 26.16 | 17.53 | 8.33 | 39.46 | 0.007 | 0.00 to 0.03 |
| SCA1:D6S202 | $-\infty$ | 4.41 | 25.80 | 26.47 | 22.12 | 14.77 | 6.51 | 26.61 | 0.08 | 0.04 to 0.14 |

[a]Z = maximum lod score, $\theta$ = recombination fraction at maximum lod score.
[b]$Z_{max}-1$ = support interval for $\theta$ (P. M. Conneally et al., Cytogenet Cell Genet 40:356–359, 1985).

USA, 86, 6686–6690 (1989)) as well as PDJ 34 (C. Breukel et. al., *Nucleic Acids Res.*, 18, 3097 (1990)). Alu-PCR fragments found to be present in R86 but absent in R78, R72, R54 and R17 were identified and were cloned into EcoRV-digested pBluescript IIKS+ plasmid (Stratagene, La Jolla, Calif.) which was modified using the T-vector protocol. See, D. Marchuk et al., *Nucleic Acids Res.*, 19, 1154 (1990). Cloned fragments were sequenced on an Applied Biosystems, Inc. (Foster City, Calif.) automated sequencer to establish STSs.

3. Isolation and Characterization of YAC clones

The Washington University library (B. H. Brownstein et al., *Science*, 244, 1348–1351 (1989)), and the CEPH library (H. M. Albertsen, et al., *Proc. Natl. Acad. Sci. USA*, 87, 4256–4260 (1990)), were screened using a PCR-based method. See, E. D. Green et. al., *Proc. Natl. Acad. Sci. USA*, 87, 1213–1217 (1990); and T. J. Kwiatkowski et. al., *Nucleic Acids Res.*, 18, 7191–7192 (1990). PCR amplifications were carried out in 25–50 µl final volume with 50 mM KCl, 10 mM Tris-HCl pH 8.3, 1.25 mM MgCl$_2$, 0.01% (w/v) gelatin, 250 µM of each dNTP; 1.25 units of Amplitaq polymerase (Perkin-Elmer/Cetus, Norwalk, Conn.) and 1 µM of each primer. PCR cycle conditions are specified in Table 6.

region. Most of the YAC clones were tested for chimerism using the Alu-PCR dot blot method described by S. Banfi et al., *Nucleic Acids Res.*, 20, 1814 (1992). The Alu-PCR products from YAC clones were hybridized to a dot-blot containing the Alu-PCR products from monochromosomal or highly reduced hybrids representing each of the 24 different human chromosomes as previously described by S. Banfi et al., *Nucleic Acids Res.*, 20, 1814 (1992). In addition a dot-blot containing Alu-PCR products from radiation reduced hybrids representing different segments of 6p was used to insure that a YAC does not contain two non-contiguous segments from 6p. Ends of YAC clones were isolated either by inverse-PCR as previously described by G. Joslyn et al., *Cell*, 66, 601–613 (1991) or by Alu-vector PCR as described by D. L. Nelson et al., *Proc. Natl. Acad. Sci. USA*, 88, 6157–6161 (1991). Alu-vector PCR was carried out using Alu-primers PDJ34 and SAL1, as described by C. Breukel et al., *Nucleic Acids Res.*, 18, 3097 (1990); and the pYAC4 vector primers described by M. C. Wapenaar et al., *Hum. Mol. Genet.*, (1993) and analagous vectors described by G. P. Bates et al., *Nature Genetics*, 1, 180–187 (1992). All YAC ends were regionally mapped by hybridization to Southern blots containing EcoRI-digested DNAs from the YAC clones and from the hybrid cell lines: I-7, R86, and R72.

TABLE 6

STSs and YACs in 6p22-p23

| Probe | Primer set | YACs[a] | Annealing temperature[b] |
|---|---|---|---|
| D6S89 | cttgttcatctgccttgtgcacct (SEQ ID NO:30) aagcgactgcctaac (SEQ ID NO:31) | B126G2, B134D5, B172B3, B214D3, C5C12, 191D8, 299B3, 379C2, 468D12, 124G2, 511H11 | 55° C. |
| AM10 (D6S335) | ttaaggaagtgttcacatcagg (SEQ ID NO:32) gaattgtgcttatgtcactggg (SEQ ID NO:33) | A23C3, A183C6, A250D5, B238F12, A91D2 | 55° C. |
| A250D5-L (D6S337) | aattctggagagaggatgttggt (SEQ ID NO:34) tcttttttggtag (SEQ ID NO:35) | 195B5, 242C5, 475A6, 30F12 | 44° C. |
| 64U | catcgtgttgtgtggtgaagctc (SEQ ID NO:36) agacgctaaactcaagg (SEQ ID NO:37) | 492H3, 172B5, 227B1, 261H7 | 50° C. |
| D6S288 | atgatccgtggtagtggcagga (SEQ ID NO:38) cctgttactgacgcc (SEQ ID NO:39) | 60H7, 351B10 | 55°s C. |
| D6S274 | ctcatctgttgaatggggatctta (SEQ ID NO:40) aatgctatgccttccg (SEQ ID NO:41) | 486F9, 149H3, 42A5, 283B2, 320E12 | 55° C. |
| FLB1 (D6S339) | tgcaaatccctcagttcacttgct (SEQ ID NO:42) tgactttgccatgttc (SEQ ID NO:43) | 140H2, 270D3, 274D12, 401D6, 57G3, 168F1 | 50° C. |
| AM12 (d6S336) | atacccatacggatttgagggc (SEQ ID NO:44) aacactatcaggctaagaatg (SEQ ID NO:45) | A71B3, 228A1, 193B3, 90A12, 539C11, 53G12, 35E8 | 55° C. |
| 53G12-L | caaataccagcaactcaccagc (SEQ ID NO:46) ggttccttcagcatcctacattc (SEQ ID NO:48) | 3G6, 82G12, 98G5, 135F6, 198C8, 330G1 | 58° C. |

[a]YACs in this study are from the CEPH and Washington University libraries. I.D. nubmers identify the library source (Washington University I.D. numbers are preceded by a letter). Several YACs were identified with more than one STS; for such information, please refer to Table 2.
[b]PCR conditions were 94° C. for 4 min followed by 35–40 cycles of 94° C. denaturation for 1 min, annealing at the specified temperature for 1 min, and 72° C. extension for 2 min. A final extension step of 7 min at 72° C. was used. PCR buffer and priemr concentrations are as described in Materials and Methods; for the 53G12-L STS a final concentration of 2% formamide was used in the PCR reaction.

Yeast DNA-agarose blocks were prepared as described by D. C. Schwartz et al., *Cell*, 37, 67–75 (1984); and G. J. B. van Ommen et al. in *Human Genetic Diseases-A Practical Approach*; K. E. Davies, ed.; pp. 113–117; IRL Press, Oxford (1986). All the YAC clones were analyzed by pulsed-field gel electrophoresis (PFGE) to determine the insert size and to confirm that a single YAC was present in a specific colony. YAC inserts were sized by electrophoresing yeast DNA through a 1% Fastlane agarose (FMC, Rockland, Me.) gel in 0.5×TAE (20 mM Tris-acetate/0.5 mM EDTA). For rapid detection of possible overlaps between YAC clones isolated at different STSs, the labelled Alu-PCR products of new YACs were hybridized to filters containing Alu-PCR products of individual YACs in the 4. Cosmid library preparation from YACs Cosmid libraries were prepared from four YAC clones; 227B1, 195B5, A250D5, and 379C2. Genomic DNA from YACs was partially digested with MboI and cloned into cosmid vector superCos 1 (Stratagene, La Jolla, Calif.) following the manufacturer's recommendations. Clones containing human inserts were identified using radiolabelled sheared human DNA as a probe.

5. Long range restriction analysis

YAC plugs were digested to completion using rare-cutter restriction enzymes as described by M. C. Wapenaar et al., *Hum. Mol. Genet.*, (1993) and analogously by G. A. Silverman et al., *Proc. Natl. Acad. Sci. USA*, 86, 7485–7489 (1989). Enzymes were purchased from New England Biolabs (Beverly, Mass.) and Boehringer Manheim Biochemicals (Indianapolis, Ind.) and were used as recommended by the manufacturer. All PFGE analyses were performed on a Bio-Rad CHEF apparatus under conditions that separate DNA fragments in the 50 kb to 600 kb range. The gels were stained with ethidium bromide, and either acid nicked or subjected to 200,000 mJ of UV energy in a UV Stratalinker 1800 (Stratagene, La Jolla, Calif.). The gels were denatured in 0.4N NaOH and transferred to Sure Blot hybridization membrane (Oncor, Gaithersburg, Md.) in either 10×SSC (1.5M NaCl/150 mM NaCitrate) or 0.4N NaOH according to the manufacturer's recommendations. Hybridizations of the filters were carried out using the probes listed in Table 6 and FIG. 6. Also pBR322 BamHI/PruII fragments of 2.5 kb and 1.6 kb specific for the left (TRP/CEN) and right (URA) pYAC4 vector arms respectively, were used. Probes were radiolabelled using the random priming technique described by A. P. Feinberg et al., "A technique for radiolabeling DNA restriction endonuclease fragments to high specific activity", Anal. Biochem., 137, 266–267 (1984); repetitive sequences were blocked using sheared human placental DNA as previously described by P. G. Sealy et al., "Removal of repeated sequences from hybridization probes", Nucleic Acids Res., 13, 1905–1922 (1985).

6. Dinucleotide repeat analysis

Primer sequences and PCR cycle conditions are presented in Table 6. Buffer conditions were the same as for Alu-PCR. All reaction volumes were 25 μl and contained 40 ng of genomic DNA. One primer of each pair was labelled at the 5' end with [$\gamma^{-32P}$] dATP. Four microliters of each reaction was mixed with 2 μl formamide loading buffer, denatured at 90°–100° C. for 3 min, cooled on ice and 4–6 μl was used for electrophoresis on a 4% polyacrylamide/7.65M urea sequencing gel.

B. Results

1. Generation of sequence tagged sites in 6p22-23 and YAC screening

Comparative analysis of the Alu-PCR products from the radiation hybrid, which retains D6S89 (R86) and from the four radiation hybrids deleted for D6S89 but retaining markers which flank D6S89 (R78, R72, R54 and R17) allowed the identification of three new DNA fragments that were present in R86 but absent in the other four. These three DNA fragments termed, AM10, AM12 and FLB1 were isolated and mapped using a 6p somatic cell hybrid panel and the radiation reduced hybrid panel (H. Y. Zoghbi et al., Genomics, 9, 713–720 (1991)) to confirm their regional localization. All three mapped to 6p and to R86 confirming their close proximity to the D6S89 locus. These three Alu-PCR fragments were subcloned and sequenced to establish sequenced tagged sites (STSs). STSs at AM10, AM12, FLB1 and D6S89 were used to screen the Washington University and the CEPH YAC libraries (H. M. Albertsen, et al., Proc. Natl. Acad. Sci. USA, 87, 4256–4260 (1990); and B. H. Brownstein et al., Science, 244, 1348–1351 (1989)). YACs isolated at these four STSs were analyzed for overlap. Insert termini from the YACs representing contig ends were isolated, subcloned and were sequenced to establish new STSs for further YAC walking. In one case an STS was established by using a subclone from a cosmid derived from a cosmid library generated for YAC 195B5.

Recently several highly informative dinucleotide repeat markers have been identified and mapped genetically by J. Weissenbach et al., Nature, 359 794–801 (1992). As discussed above, two markers, D6S274 and D6S288 were found to map within the SCA1 critical region and were subsequently used to screen the YAC libraries. Using the STSs listed in Table 6, YAC clones were isolated.

2. Characterization of YAC clones

The sizes of the YAC inserts were determined by pulsed-field gel electrophoresis (PFGE); insert sizes ranged from 75–850 kb. Given the high frequency of insert chimerism, an Alu-PCR based hybridization strategy for rapid detection of chimerism, as described by S. Banfi et al., Nucleic Acids Res., 20, 1814 (1992) was used. Thirty of the YAC clones were tested using this approach and eight (27%) were found to be chimeric. Insert ends isolated from YACs determined to be non-chimeric by the dot blot hybridization approach mapped to 6p22-23 with the exception of the two ends from 198C8 which proved to map to other chromosomes.

Two approaches were used, inverse-PCR (G. Joslyn et al., Cell, 66, 601–613 (1991)) and Alu-PCR (analogous to that described by D. L. Nelson et al., Proc. Natl. Acad. Sci. USA, 86, 6686–6690 (1989)) to isolate YAC ends. In total, 34 YAC ends were isolated; inverse-PCR yielded 26 ends and Alu-vector PCR yielded 8 ends. To isolate the left end of the 195B5 YAC we screened a cosmid library prepared from this YAC using pYAC4 left end sequences (S. K. Bronson et al., Proc. Natl. Acad. Sci. USA, 88, 1676–1680 (1991)) as a probe. This approach was taken because inverse-PCR yielded an end which was predominantly an Alu-containing sequence and Alu-PCR failed in yielding an end. Cosmid clone A32 was found to contain the left end of 195B5 and a subclone, 64U, was used to establish an STS for further YAC library screenings.

In order to confirm the 6p22-23 regional origin of all YAC ends or subclones, these fragments were used as probes against Southern blots containing EcoRI-digested DNAs from a somatic cell hybrid retaining 6p (I-7), from radiation reduced hybrids known to retain fragments of 6p (H. Y. Zoghbi et al., Genomics, 9, 713–720 (1991)) and from the YAC clones at a particular STS.

3. Probe content mapping of YACs

In order to define the degree of overlap between the clones and to detect possible rearrangements such as internal deletions of the YACs, a probe content mapping strategy was used based on: 1) PCR analysis of all the clones using all the STSs in the region including both the ones described in Table 6, and those at highly informative dinucleotide repeats such as AM10-GA and SB1; and 2) hybridization of Southern blots containing EcoRI-digested DNAs from YACs in the relevant region, with densely-spaced DNA probes derived from YAC ends, cosmids subclones of YACs, or Alu-PCR fragments from YACs. The results of this analysis for a representative subset of the YACs (32 clones) are summarized in Table 7. Thirty-nine YAC clones form an uninterrupted YAC contig from D6S274 to 82G12-R (right end of YAC clone 82G12). Other than an internal deletion in one YAC (351B10) no other deletions were detected within the resolution of this analysis; furthermore the extent of chimerism for some YAC clones (such as 270D12 and 140H2) was determined. The centromere-telomere orientation of the YAC contig on 6p was determined using both genetic data as well as physical mapping data. Using dinucleotide repeats analysis at D6S109, AM10GA, D6S89, and SB1 in the key individual with recombination event between D6S89 and SCA1 revealed that the recombination event occurred between AM10GA and D6S89. Given that D6S109 is centromeric to D6S89, the recombination analysis suggests that AM10GA is centromeric to D6S89. The centromere-telomere position of SB1 with respect to D6S89 could not be determined genetically.

TABLE 7

Characterization of YACs using 6p22-p23 STSs and YAC fragments

| YAC | Size (kb) | Chimerism | D6S274 | 60H7Lg | D6S288 | 64U | A25005-L | AM10-GA | AM10 | 168F1-R | C5C12-R |
|---|---|---|---|---|---|---|---|---|---|---|---|
| 149H3 | 345 | N | + | + | − | − | − | | | | |
| 60H7 | 580 | N | + | + | + | − | − | | | | |
| 351B10 | 330 | N | + | − | + | − | − | | | | |
| 227B1 | 560 | N | + | + | + | + | − | | | | |
| 172B5 | 345 | Y | − | − | + | + | − | | | | |
| 195B5 | 365 | N | − | | − | + | + | − | − | | − |
| 475A6 | 365 | N | | | | − | + | − | − | | − |
| 242C5 | 340 | N | | | | − | + | + | + | − | − |
| A250D5 | 250 | N | | | | − | + | + | + | − | − |
| A23C3 | 530 | Y | | | | − | − | − | + | − | − |
| A18306 | 120 | N | | | | − | − | − | + | − | − |
| B238F12 | 390 | Y | | | | − | − | + | + | − | − |
| A91D2 | 325 | N | | | | − | − | − | + | − | − |
| 191D8 | 650 | N | | | | | | − | + | + | + |
| 379C2 | 575 | N | | | | | | − | + | + | + |
| C5C12 | 75 | N | | | | | | − | − | − | + |
| B214D3 | 200 | N | | | | | | | − | − | − |
| 299B3 | 375 | N | | | | | | − | − | + | + |
| 468D12 | 280 | N | | | | | | | − | + | + |
| 168F1 | 400 | N | | | | | | | − | + | + |
| 270D3 | 650 | Y | | | | | | | − | − | + |
| 274D12 | 240 | N | | | | | | | − | − | − |
| 140H2 | 440 | Y | | | | | | | − | − | − |
| 57G3 | 400 | N | | | | | | | − | − | − |
| 401D6 | 340 | N | | | | | | | − | − | − |
| 193B3 | 850 | | | | | | | | | | |
| 228A1 | 350 | | | | | | | | | | |
| 90A12 | 650 | | | | | | | | | | |
| 35E8 | 400 | | | | | | | | | | |
| 53G12 | 370 | | | | | | | | | | |
| 135F6 | 400 | | | | | | | | | | |
| 82G12 | 380 | | | | | | | | | | |

| YAC | Size (kb) | D6S89 | B214D3-R | FLB1 | 53G12-R | 401D6-R | AM12 | 135F6-L | 53G12-L | 135F6-R | 83G12-R |
|---|---|---|---|---|---|---|---|---|---|---|---|
| 149H3 | 345 | | | | | | | | | | |
| 60H7 | 580 | | | | | | | | | | |
| 351B10 | 330 | | | | | | | | | | |
| 227B1 | 560 | | | | | | | | | | |
| 172B5 | 345 | | | | | | | | | | |
| 195B5 | 365 | | | | | | | | | | |
| 475A6 | 365 | | | | | | | | | | |
| 242C5 | 340 | | | | | | | | | | |
| A250D5 | 250 | − | − | − | | | | | | | |
| A23C3 | 530 | − | − | − | | | | | | | |
| A18306 | 120 | − | − | − | | | | | | | |
| B238F12 | 390 | − | − | − | | | | | | | |
| A91D2 | 325 | − | − | − | | | | | | | |
| 191D8 | 650 | + | + | − | | | | | | | |
| 379C2 | 575 | + | + | − | | | | | | | |
| C5C12 | 75 | + | − | − | | | | | | | |
| B214D3 | 200 | + | + | − | | | | | | | |
| 299B3 | 375 | + | + | + | | | | | | | |
| 468D12 | 280 | + | + | − | | | | | | | |
| 168F1 | 400 | + | | + | + | − | − | | | | |
| 270D3 | 650 | − | + | + | + | − | − | | | | |
| 274D12 | 240 | − | + | + | + | − | − | | | | |
| 140H2 | 440 | − | − | + | + | − | − | | | | |
| 57G3 | 400 | − | | + | + | + | − | | | | |
| 401D6 | 340 | − | + | + | + | + | − | | | | |
| 193B3 | 850 | | | − | − | + | + | − | − | − | − |
| 228A1 | 350 | | | − | − | + | + | − | − | − | − |
| 90A12 | 650 | | | − | − | + | + | − | − | − | − |
| 35E8 | 400 | | | − | + | + | + | + | + | − | − |
| 53G12 | 370 | | | − | + | + | + | + | + | − | − |
| 135F6 | 400 | | | | | | | + | + | + | − |
| 82G12 | 380 | | | | | | | − | + | + | + |

Note.
(+) = present, (−) = absent; Y/N = chimerism is/not detected. YAC ends are identified by YAC names followed by L or R for left or right.

Physical mapping, using both radiation hybrids and YACs, was carried out to resolve the centromere-telomere order of the loci. The radiation reduced hybrids R17 and R72 are known to contain markers centromeric to D6S89; these markers include D6S108 and D6S88 which map centromeric to D6S109. See, H. Y. Zoghbi et al., *Genomics*, 9, 713–720

(1991). R72 also retains D6S109, but a small gap in R17 was revealed as this radiation hybrid did not retain D6S109, but was positive for an end isolated from a YAC at the D6S109 locus. Analysis of the radiation reduced hybrids revealed that D6S274 and D6S288 are present in R17, R72 and R86, whereas AM10GA, D6S89, and SB1 are present only in R86 (FIG. 5). Furthermore, STS content mapping with D6S260 and D6S289, two dinucleotide repeats that are telomeric to D6S288 (J. Weissenbach et al., Nature, 359 794–801 (1992)), revealed that D6S260 is present in the same YACs as D6S89 and SB1 (379C2 and 168F1), and that D6S289 is present in 57G3 and 35E8 two YACs derived using the FLB1 and AM12 STS respectively. These data, confirm that the order of the loci as well as the centromere-telomere orientation of the YAC contig presented in FIG. 6 is correct.

Figure 6:
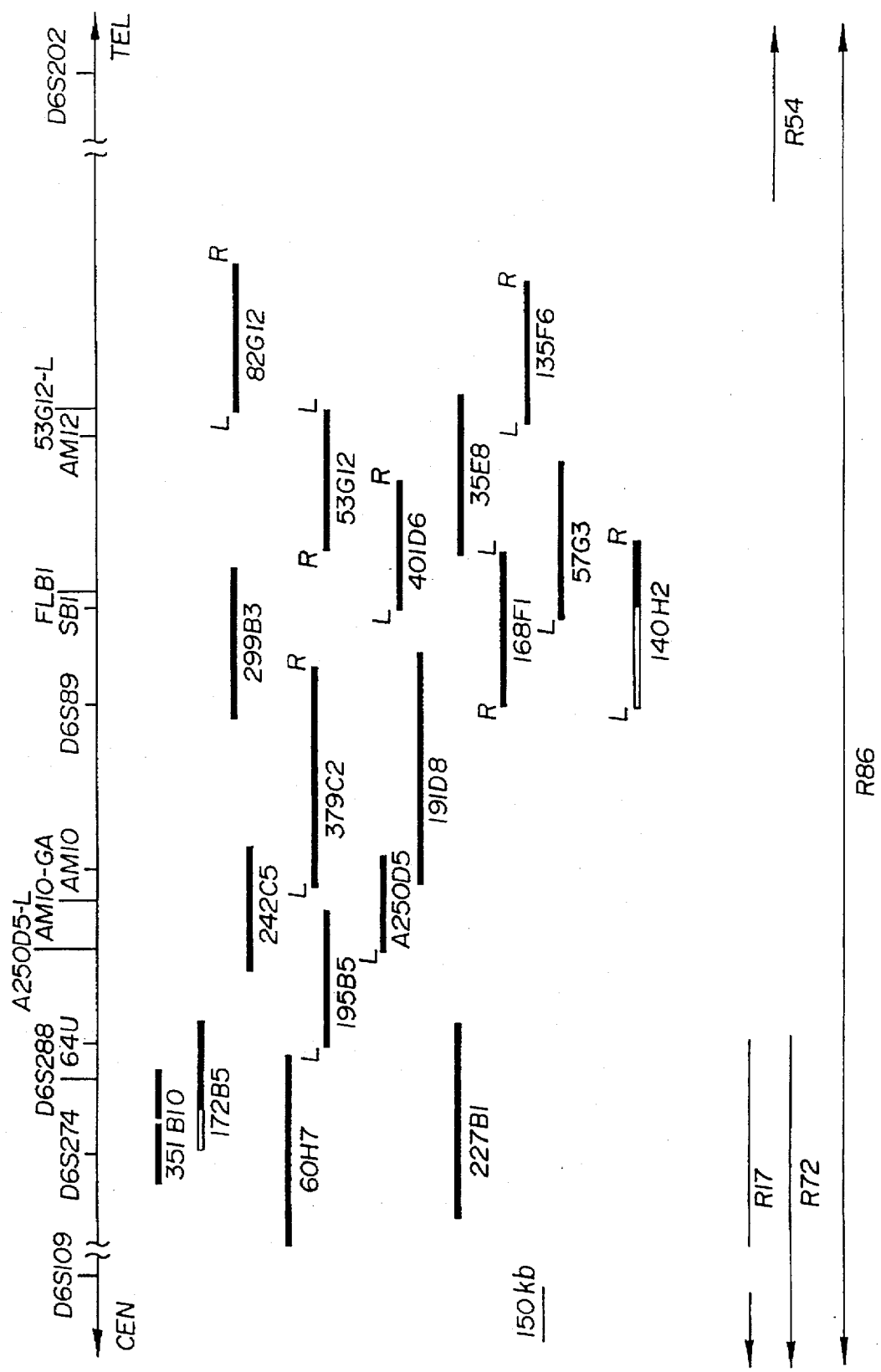
FIG. 6. A schematic diagram of 6p22-23 region showing the new markers and the YAC contig. At the bottom of the diagram, the radiation hybrid reduced panel used for regional mapping is shown. YAC clones are represented as dark lines, open segments indicate a noncontiguous region of DNA. The discontinuity shown in YAC clone 351B10 indicate that this YAC has an internal deletion. All of the ends of the YAC clones that were isolated are designated by an "L" for the left end or an "R" for the right end.

FIG. 6 shows a selected subset of YAC clones which span the entire contig from D6S274 to 82G12-R. A minimal number of 8 YACs spans this region. The positions of the STSs which were used to isolate the YACs are also shown. Based on the size of the YACs and the degree of overlap, this contig is estimated to span 2.5 Mb of genomic DNA in 6p22-23 with D6S89 located approximately in the middle.

4. Delineating the SCA1 critical region

Figure 7:
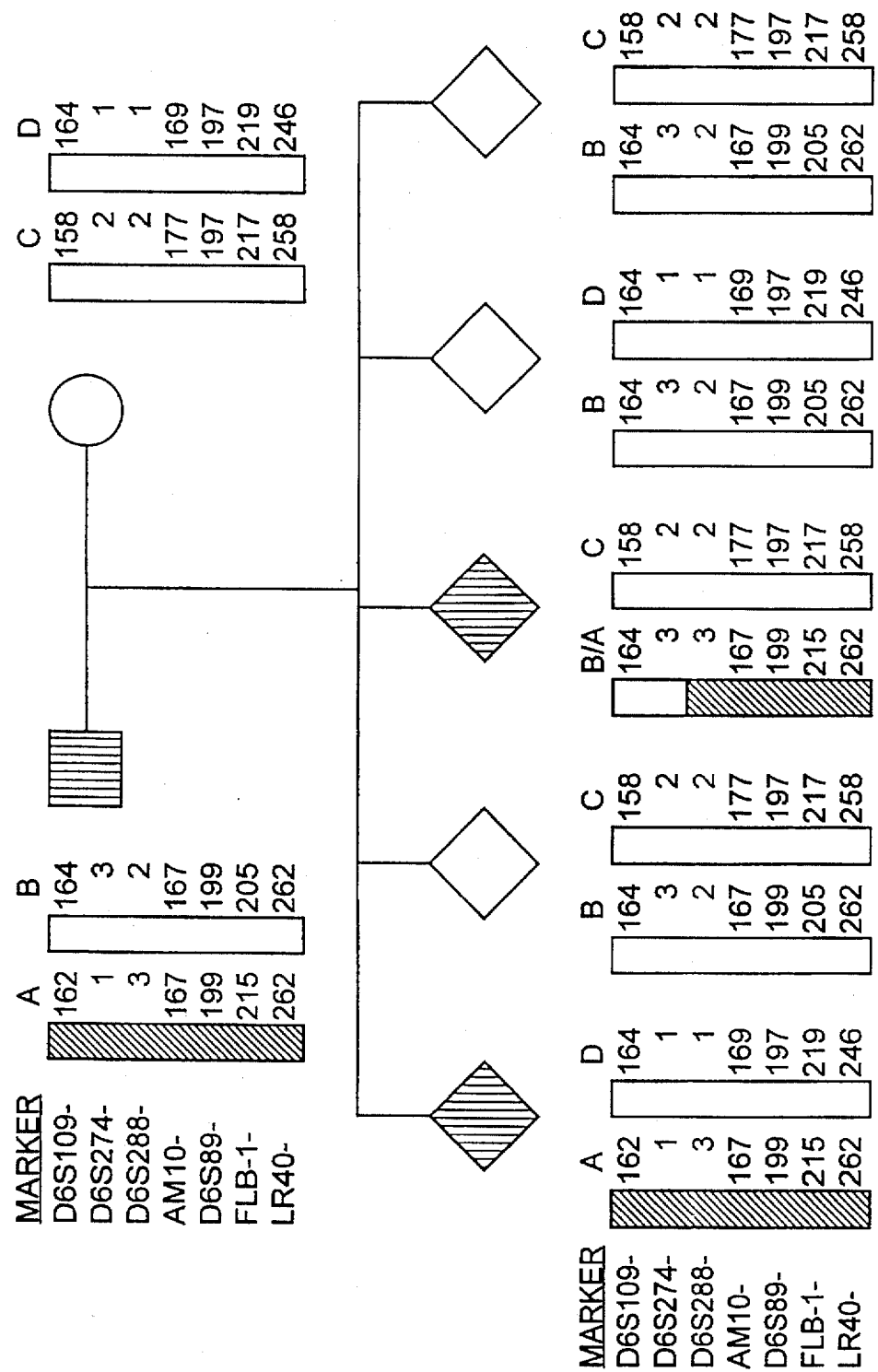
FIG. 7. Genotypic data for 6p22-23 dinucleotide repeat markers are shown for a reduced pedigree from the MN-SCA1 kindred. This figure summarizes a second recombination event that led to the precise mapping of the SCA1 locus.
Figure 8:
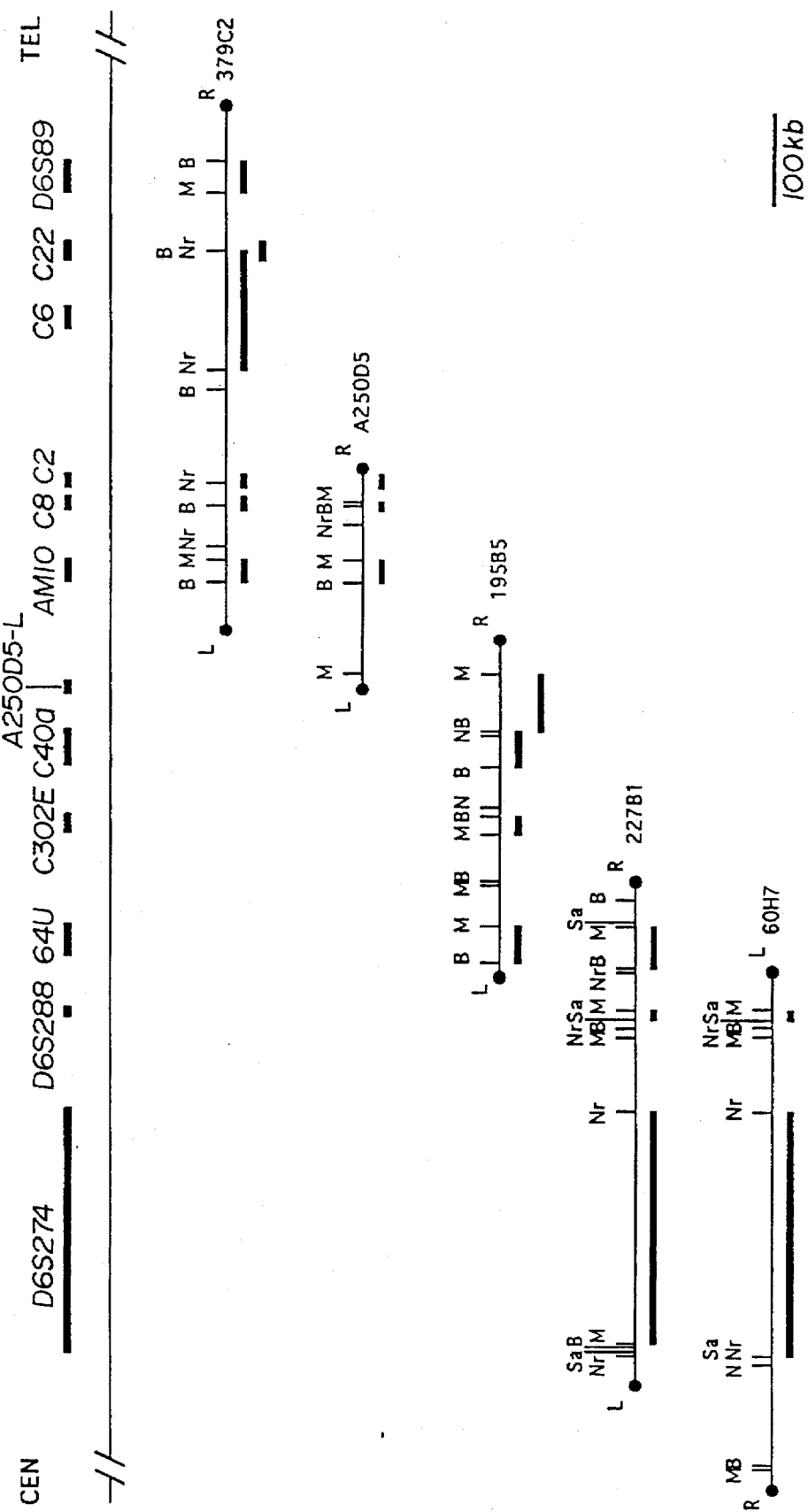
FIG. 8. Long-range restriction maps of YACs, 227B1, 60H7, 195B5, A250D5, and 379C2. YACs 351B10, 172B5, 172B5, and 168F1 were also used in the restriction analysis (data not shown). The restriction sites are marked as N, NotI; B, BssHII; Nr, NruI; M, MluI, S, SacII, and Sa, SalI. A summary map of the SCA1 gene region with the position of the DNA markers used as probes (boxes) is shown. The centromere-telomere orientation is indicated by cen/tel respectively.

Genetic studies using recently identified dinucleotide repeats (AM10GA and SB1) showed that SCA1 maps centromeric to the D6S89 locus very close to AM10GA (peak load score of 42.1 at a recombination frequency of zero) in nine large SCA1 kindreds. Thus D6S89 is the closest flanking marker at the telomeric end. Previously, the closest flanking marker at the centromeric end was D6S109, a dinucleotide repeat estimated to be 6.7 cM centromeric to D6S89. To identify a closer flanking marker at the centromeric end, we mapped D6S260, D6S274, D6S288 and D6S289, four dinucleotide repeat-containing markers known to map 6p22-23 (J. Weissenbach et al., Nature, 359 794–801 (1992)). The regional mapping of these markers was done using radiation reduced hybrids and the YAC clones isolated from this region. These data revealed that D6S274 and D6S288 map centromeric to AM10GA as evident by amplification of DNA from radiation hybrids R17 and R72 which are known to be centromeric to AM10GA. Genotypical analysis of the DNAs from individuals with key recombination events between D6S109 and D6S89 as well as from affected and normal individuals (to establish chromosomal phase) from the five SCA1 kindreds (MN-SCA1, MI-SCA1, TX-SCA1, M-SCA1 and MS-SCA) was carried out. This analysis revealed no recombination between D6S288 and SCA1. A single recombination event between D6S274 and D6S288 was detected in individual MN-1 from the MN-SCA1 kindred (FIG. 7); this individual was one of the six individuals identified above as having a recombination event between SCA1 and D6S109. This analysis allowed us to identify D6S274 as the closest flanking marker at the centromeric end. These data combined with that discussed above determined that the SCA1 critical region maps between D6S274 and D6S89. This region is cloned in a minimum of four overlapping and non-chimeric YACs as shown in FIG. 8.

5. Long-range restriction mapping

In order to have an estimate of the size of the YAC contig in the SCA1 critical region we performed long-range restriction analysis on YACs from this region. The YACs used for this analysis included: 227B1, 60H7, 351B10, 172B5, 195B5, A250D5, 379C2, and 168F1. The following rare-cutter restriction enzymes were used: NotI, BssHII, NruI, MluI, SacI and SalI. Restriction fragments separated by PFGE and transferred onto nylon membranes, were detected by sequential hybridizations of the filter to several DNA probes which included: DNA probes specific for the left and right arm of the pYAC4 vector; insert termini for internal YAC clones; internal probes and cosmid subclones; and an Alu-specific probe. The position and names of all the probes used in the long-range restriction analysis is shown in FIG. 8. Based on this analysis the internal deletion for YAC 351B10 was confirmed. The extent of overlap between the YAC clones was determined. The size of the critical SCA1 region was estimated to be 1.2 Mb. Internal deletions and/or other rearrangements could not be excluded for the areas where a single YAC was analyzed by restriction enzyme analysis. These include approximately a 220 kb region of 195B5 and a 335 kb region of 379C2.

III. Expansion of an Unstable Trinucleotide Repeat in SCA1

A. Methods

1. Genomic Southern Blotting Using 3.36 EcoRI Fragment

Genomic DNA from YACs was partially digested with MboI and cloned into cosmid vector super Cos1 (Strategene, La Jolla, Calif.) following the manufacturer's protocol. Clones containing human inserts were identified by hybridization with radiolabeled human DNA and were arrayed on a gridded plate. Filter lifts were screened for the presence of trinucleotide repeats by hybridization of $[\gamma-^{32p}]$ end-labeled $(GCT)_7$ oligonucleotide. Twenty-three positive cosmids were identified and all were found to be overlapping and to contain the same 3.36-kb EcoRI fragment which hybridized to the $(GCT)_7$ probe and ultimately proved to have the CAG repeat by sequence analysis.

2. PCR Amplification of $(CAG)_n$ Region

Fifty ng of genomic DNA was mixed with 5 pmol of each primer (CAG-a/GAG-b or Rep-1/Rep-2) in a total volume of 20 µl containing 1.5 mM $MgCl_2$, 300 µM dNTPs (1.25 mM $MgCl_2$ and 250 µM dNTPs for Rep-1/Rep-2 primers), 50 mM KCl, 10 mM Tris-HCl pH 8.3, and 1 unit of Amplitaq (Perkin Elmer-Cetus, Norwalk, Conn.). For the CAG-a/CAG-b primer pair $[\alpha-^{32}p]dCTP$ was incorporated in the PCR reaction, for Rep-1/Rep2 primer pair the Rep-1 primer was labeled at the 5' end with $[\gamma-^{32P}]dATP$. Formamide was used at a final concentration of 2% when using the Rep-1/Rep-2 primer pair. Samples, overlaid with mineral oil, were denatured at 94° C. for 4 minutes followed by 30 cycles of denaturation (94° C., 1 min.), annealing (55° C., 1 min.), and extension (72° C., 2 min.). Six microliters (µl) of each PCR reaction was mixed with 4 µl formamide loading buffer, denatured at 90° C. for 2 min., and electrophoresed through a 6% polyacrylamide/7.65M urea DNA sequencing gel. Allele sizes were determined by comparing migration relative to an M13 sequencing ladder.

B. Results

Figure 9:
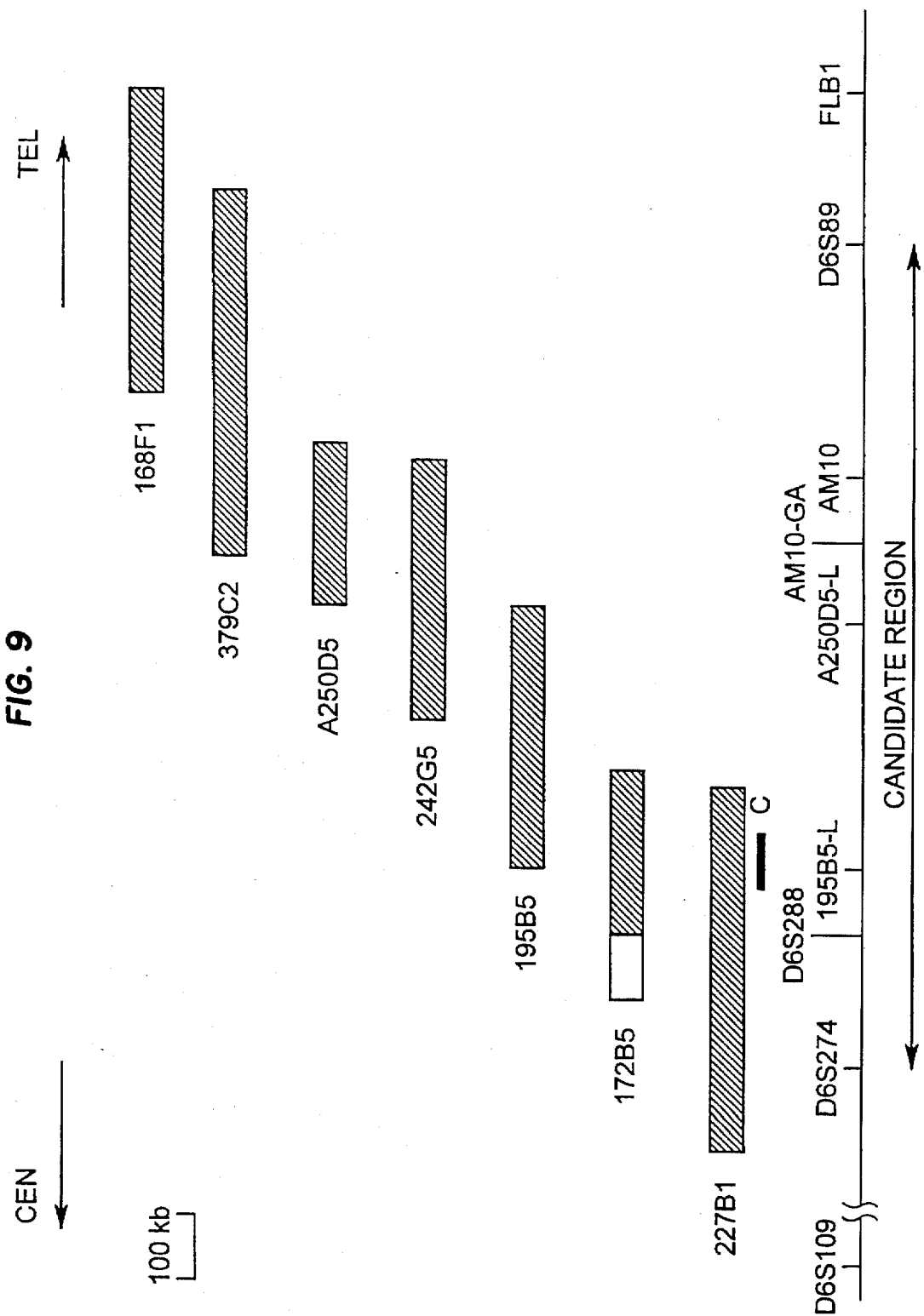
FIG. 9. Physical map of the SCA1 region. The positions of various genetic markers and sequence tagged sites (STSs) relative to the overlapping YAC clones are shown. AM10 and FLB1 are STSs developed using a radiation reduced hybrid retaining chromosome 6p22-23, A205D5-L and 195B5-L are STSs from insert termini of YACs A250D5 and 195B5. D6S89, D6S109, D6S288 and D6S274, and AM10-GA are dinucleotide repeat markers used in the genetic analysis of SCA1 families. The SCA1 candidate region is flanked by the D6S274 and D6S89 markers which identify the closest recombination events. The YAC clones shown here are indicated by the cross-hatched markings. YAC 172B5 has two non-contiguous segments of DNA as indicated by the open bar for the non-6p segment. The YACs are designated according to St. Louis and CEPH libraries. The position of the cosmid contig (C) which contains the overlapping cosmids which are $(CAG)_n$ positive is indicated by a solid black bar. The overlap between the YACs was determined by long-range restriction analysis. Orientation is indicated as centromeric (Cen) and telomeric (Tel).

As discussed above, in efforts to clone the SCA1 gene, key recombination events were analyzed using several dinucleotide repeat polymorphisms mapping to 6p22-23 to identify the minimal region likely to contain the SCA1 gene. This analysis revealed that there were no recombination events between SCA1 and the centromeric marker D6S288 in five large kindreds or between SCA1 and the telomeric marker AM10GA in nine large kindreds. A single recombination event was detected between D6S274 and D6S288 identifying the closest flanking marker at the centromeric end to be D6S274. At the telomeric end, a single recombination event was detected between AM10GA and D6S89 and identified the latter as the flanking marker. A yeast artificial chromosome (YAC) contig extending from D6S274 to D6S89 and spanning the entire SCA1 candidate region was developed. A subset of the YAC clones encompassing this region is shown in FIG. 9. Long-range restriction analysis determined the size of the SCA1 candidate region to be approximately 1.2 Mb. Cosmid libraries were constructed from YACs 227B1, 195B5, A250D5, and 379C2. Arrays of cosmid clones containing human inserts were hybridized with an oligonucleotide consisting of tandemly repeated CAG, as well as with oligonucleotides containing other trinucleotide repeats. Several hybridizing cosmid clones were identified, 23 of which were positive for the CAG repeat and mapped to the region between D6S288 and AM10GA (FIG. 9). All 22 of these clones shared a common 3.36-kb EcoRI fragment that specifically hybridized to the CAG repeat.

Figure 10A:
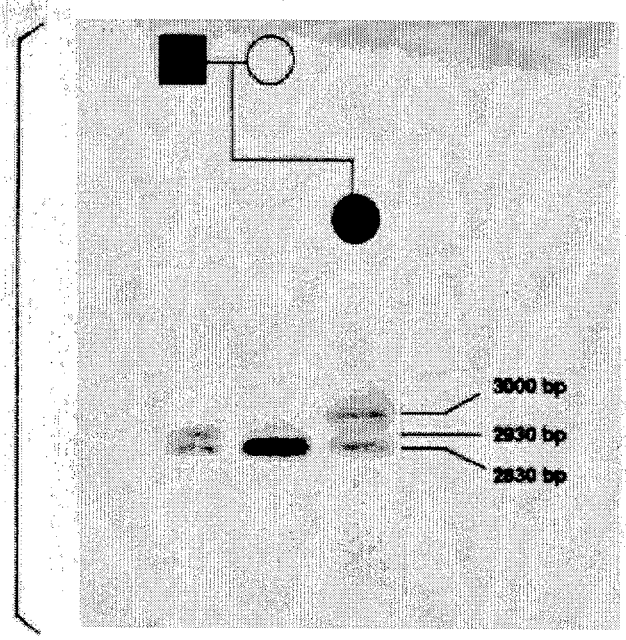
FIGS. 10A–10C. Southern blot analysis of leukocyte DNA using the 3.36-kb EcoRI fragment which contains the repeat as a probe.
Figure 10B:
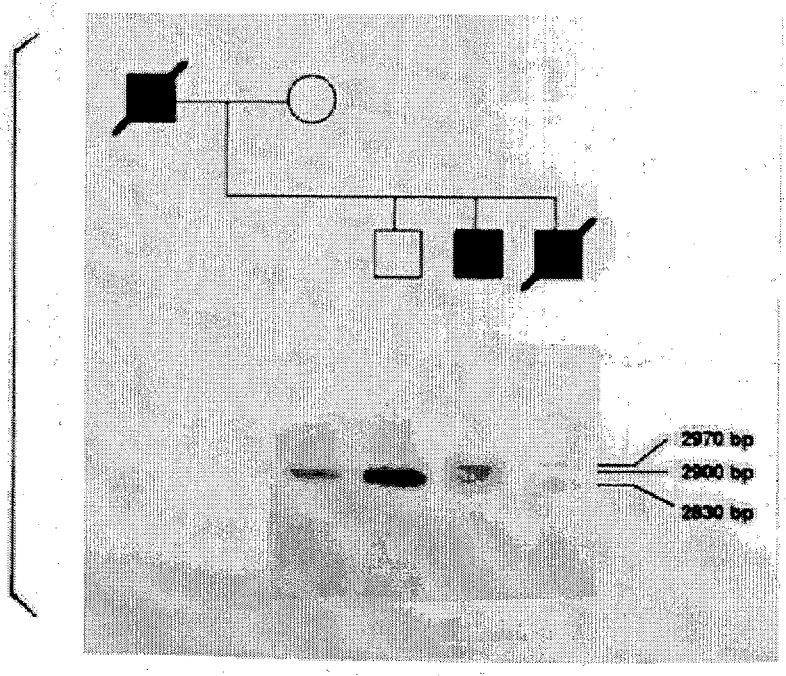
Figure 10C:
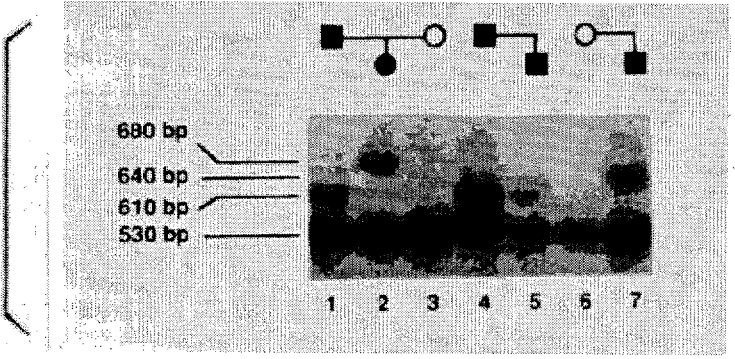

To test the genetic stability of this repeat in SCA1, we used Southern blotting analysis to examine families with juvenile onset SCA1. A two-generation reduced pedigree from the TX-SCA1 family is shown in FIG. 10a. Paternal transmission of SCA1 with an expansion of a TaqI fragment was noted. A 2830-bp fragment was detected in DNA from the unaffected spouse and on the normal chromosome from SCA1 patients, whereas a 2930-bp fragment was found in DNA from the affected father (onset at 25 years) and a3000-bp fragment was detected in DNA from his affected child with an onset at 4 years. In a second SCA1 kindred, family MN-SCA1 (FIG. 10b), two offspring inherited SCA1 from their father and differed in their age at onset (25 years and 9 years). These individuals also differ in the size of the amplified TaqI fragment they inherited from their affected father, 2900-bp and 2970-bp, respectively. Enlargement of the $(CAG)_n$-containing fragment on SCA1 chromosomes from the same TX-SCA1 juvenile onset family was also demonstrated by Southern analysis following BstNI digestion. The BstNI fragment is 530-bp on normal chromosomes, is 610-bp in the SCA1 affected father, and is 680-bp in the affected juvenile onset offspring (FIG. 10c). In each of these families, nonpaternity was excluded by genotypic analysis with a large number (greater than 10) of dinucleotide repeat markers. In addition, the size of the $(CAG)_n$-containing TaqI fragment in DNA from 30 unaffected spouses was compared to the sizes of the repeat containing TaqI fragment in DNA from 62 individuals affected with late-onset SCA1. The affected individuals are from five different SCA1 families: LA-SCA1, MI-SCA1, MN-SCA1, MS-SCA1, and TX-SCA1. In all 30 unaffected spouses fragment sizes were approximately 2830-bp and no expansions or reductions were detected with transmission to offspring (data not presented). In contrast, DNA from 58 of the 62 SCA1 affected individuals contained detectably expanded TaqI fragments ranging in size from 2860-bp to 3000-bp in addition to the 2830-bp fragment. The DNAs from the remaining four individuals were found to have an expansion when analyzed by polymerase chain reaction (PCR). The expanded fragment always segregated with disease, and in some cases the fragment expanded further in successive generations. In the juvenile cases the expanded restriction fragment was larger than that in the affected parent (uniformly the father in the cases analyzed) supporting the conclusion that a DNA sequence expansion is the mutational basis of SCA1.

To identify the region involved in the DNA expansion, a 500-bp $(CAG)_n$-containing subclone of the 3.36-kb EcoRI fragment was sequenced (FIG. 3), as was the entire 3.36-kb fragment (FIG. 1). This normal allele demonstrated 30 CAG repeat units. In two of the repeat units (position 13 and 15) a T was present instead of a G.

Figure 11A:
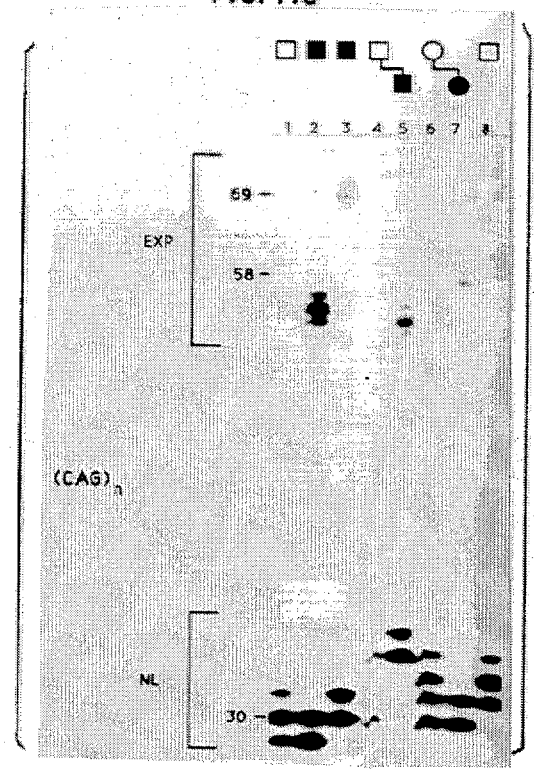
FIGS. 11A–11B. Analysis of the PCR-amplified products containing the trinucleotide repeat tract in normal and SCA1 individuals. The CAG-a/CAG-b primer pair was used in panel (a) whereas the Rep-1/Rep-2 primer pair was used in panel (b). The individuals in lanes 1, 2 and 3 in panel (a) are brothers. The range for the normal (NL) and expanded (EXP) $(CAG)_n$ repeat units is indicated.
Figure 11B:
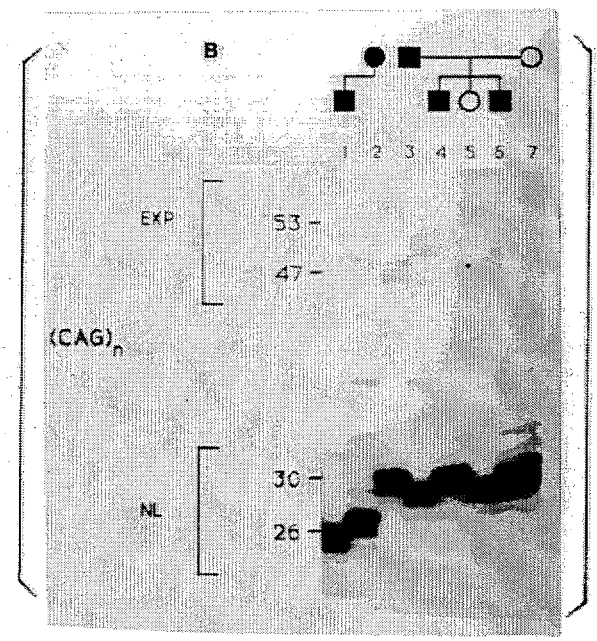
Figure 12:
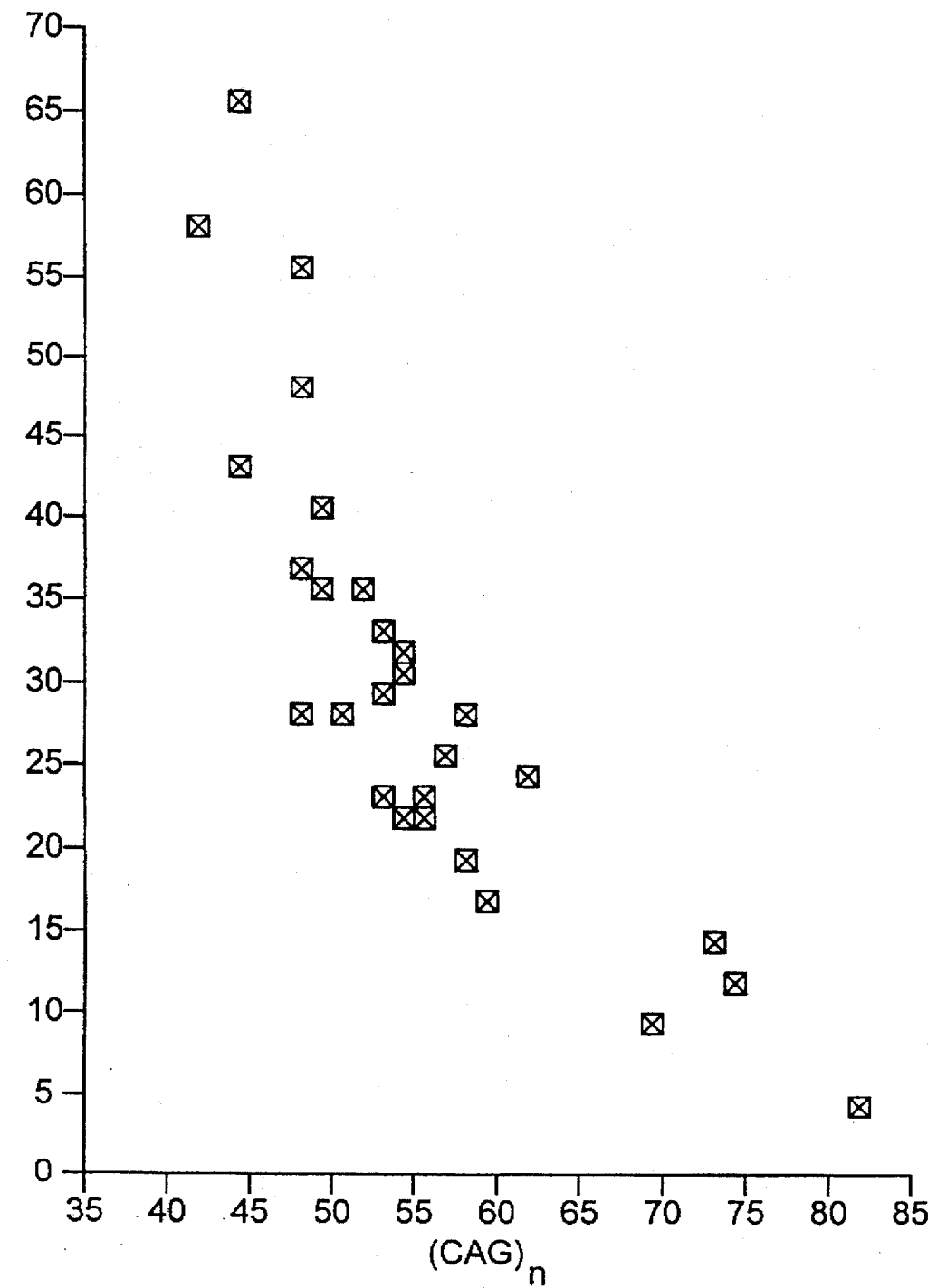
FIG. 12. A scatter plot for the age-at-onset in years versus the number of the $(CAG)_n$ repeat units is shown to demonstrate the correlation between the age-at-onset and the size of the expansion. A linear correlation coefficient of −0.845 was obtained. In addition a curvilinear correlation coefficient was calculated given the non-linear pattern of the plot. The curvilinear correlation coefficient is −0.936.

To confirm that the CAG repeats were involved in the observed length variation, we analyzed the size of PCR-amplified fragments in 45 unaffected spouses and 31 SCA1 affected individuals using synthetic oligonucleotides that flank the CAG repeat. One pair of primers (CAG-a/CAG-b) was located within 9-bp of the repeats and identified length variation indicating that the CAG repeats are the basis of the variation. Normal individuals displayed 11 alleles ranging from 25 to 36 repeat units (Table 8). Heterozygosity in normal individuals was 84%. Examination of this sequence in 31 individuals affected with SCA1 demonstrated that each was a heterozygote with one allele within the size range seen in the normal individuals and a second expanded allele within a range of 43 to 81 repeat units (FIG. 11). Late onset SCA1 individuals showed at least 43 repeats, while 59–81 units were found in the juvenile cases. FIG. 12 depicts correlation between the age-at-onset and the number of the repeat units. A linear correlation coefficient (r) of −0.845 was obtained indicating that 71.4% ($r^2$) of the variation in the age-at-onset can be accounted for by the number of $(CAG)_n$ repeat units. The largest trinucleotide repeat expansion was noted in SCA1 patients with juvenile onset who typically had a more rapid course. It is of interest that all of these patients were offspring of affected males, which is reminiscent of Huntington disease where there is preponderance of male transmission in juvenile cases.

The expansion of the trinucleotide repeat was observed in all affected individuals examined by PCR from five different kindreds representing at least two ethnic backgrounds, American Black and Caucasian. Genotypic analysis using DNA markers that are very closely linked to SCA1 (D6S274, D6S288, AM10GA, D6S89 and SB1) revealed that there are four haplotypes segregating with disease among the five families analyzed.

Sequence analysis of the fragment containing the CAG repeat indicated that there are several extended open reading frames. Translation of the repeat in one of these frames (389-bp) would encode polyglutamine.

TABLE 8

Comparison of the number of CAG repeat units on normal and SCA1 chromosomes

| Number of Repeats | Normal Chromosomes | | SCA1 Chromosomes | |
|---|---|---|---|---|
| | Number | Frequency | Number | Frequency |
| ≧60 | 0 | 0 | 4 | 0.13 |
| 50–59 | 0 | 0 | 17 | 0.55 |
| 43–49 | 0 | 0 | 10 | 0.32 |
| 37–42 | 0 | 0 | 0 | 0 |
| 35–36 | 1 | 0.01 | 0 | 0 |
| 30–34 | 49 | 0.55 | 0 | 0 |
| ≦29 | 40 | 0.44 | 0 | 0 |
| TOTAL | 90 | 1.00 | 31 | 1.00 |

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for identifying individuals at risk for developing spinocerebellar ataxia type 1 comprising the step of:
analyzing the CAG repeat region of a spinocerebellar ataxia type 1 gene wherein individuals at risk for developing spinocerebellar ataxia type 1 have greater than or equal to 43 CAG repeats.

2. The method of claim 1 wherein the analyzing step further comprises the steps of:
digesting genomic DNA with at least one restriction endonuclease to obtain DNA fragments;
separating the DNA fragments on a gel;
probing the DNA fragments with a probe capable of binding to the CAG repeat region;
detecting probe binding to the CAG repeat region.

3. The method of claim 2 comprising the additional step of:
sequencing the CAG repeat region.

4. The method of claim 1 wherein the analyzing step comprises the steps of:

performing a polymerase chain reaction with oligonucleotide primers capable of amplifying the CAG repeat region located within the spinocerebellar ataxia type 1 gene; and detecting amplified DNA fragments containing the CAG repeat region.

5. A DNA fragment produced by the method of claim 4 wherein the DNA fragment contains a CAG repeat region and wherein the DNA fragment specifically hybridizes to a spinocerebellar ataxia type 1 gene.

6. The method of claim 4 comprising the additional step of sequencing the amplified DNA fragments.

7. The method of claim 4 wherein the oligonucleotide primers are selected from the group consisting of CCGGAGCCCTGCTGAGGT (SEQ ID NO:8), CCAGACGCCGGGACAC (SEQ ID NO:9), AACTGGAAATGTGGACGTAC (SEQ ID NO:10), CAACATGGGCAGTCTGAG (SEQ ID NO:11), CCACCACTCCATCCCAGC (SEQ ID NO:12), TGCTGGGCTGGTGGGGGG (SEQ ID NO:13), CTCTCGGCTTTCTTGGTG (SEQ ID NO:14), and GTACGTCCACATTTCCAGTT (SEQ ID NO:15).

8. The method of claim 1 wherein an individual not at risk for developing spinocerebellar ataxia type 1 has less than or equal to 36 CAG repeats.

9. An isolated DNA fragment having a sequence comprising bases 1716–1749 of SEQ ID NO:1 of a spinocerebellar ataxia type 1 gene and a CAG repeat region.

10. The isolated DNA fragment of claim 9, wherein the CAG repeat region is optionally interrupted with CAG trinucleotides.

11. The isolated DNA fragment of claim 9, wherein there are at least 43 CAG repeats in the CAG repeat region.

12. The isolated DNA fragment of claim 10, wherein there are less than or equal to 36 CAG repeats in the CAG repeat region.

13. Isolated oligonucleotide primers selected from the group consisting of CCGGAGCCCTGCTGAGGT (SEQ ID NO:8), CCAGACGCCGGGACAC (SEQ ID NO:9), AACTGGAAATGTGGACGTAC (SEQ ID NO:10), CAACATGGGCAGTCTGAG (SEQ ID NO:11), CCACCACTCCATCCCAGC (SEQ ID NO:12), TGCTGGGCTGGTGGGGGG (SEQ ID NO:13), CTCTGGCTTTCTTGGTG (SEQ ID NO:14), and GTACGTCCACATTTCCAGTT (SEQ ID NO:15) useful for detecting spinocerebellar ataxia type 1.

* * * * *

UNITED STATES PATENT AND TRADEMARK OFFICE
CERTIFICATE OF CORRECTION

PATENT NO. : 5,741,645
DATED : April 21, 1998
INVENTOR(S) : Harry T. Orr et al.

It is certified that error appears in the above-identified patent and that said Letters Patent is hereby corrected as shown below:

Column 1,
Second H.G. Harley et al. entry, delete "*Lancet, 139*" and insert -- *Lancet*, 339 --;

Column 4,
Line 31, delete "6p22-23" and insert -- 6p22-p23 --;
Line 39, delete "fight end" and insert -- right end --;
Line 40, delete "6p22-23" and insert -- 6p22-p23 --;
Line 58, delete "6p22-23" and insert -- 6p22-p23 --;

Column 10,
Line 47, delete "palmer" and insert -- primer --;

Column 13,
Line 2, of footnote 1, delete "for B1," and insert -- for SB1 --;
Line 3, of footnote 1, delete "$LR_{40}$, $A_1$=241bp" and insert -- LR40, TXSCA1 $A_1$=241 bp --;
Line 4, of footnote 1, delete $A_1^1$=154 bp" and insert -- $A_1$=154 bp --;

Column 15,
Table 4, 1st entry under column entitled Relative Odds, delete "$2 \times 10^1$" and insert -- $2 \times 10^8$ --;
Table 5, 3rd entry under column entitled Support Interval, delete "0.00 to 0.002" and insert -- 0.00 to 0.02 --;
Table 5, add the following line between the SCA1:SB and SCA1:D6S202 entries:
-- SCA1:LR40  -∞  27.80  31.77  29.73  23.61  16.11  7.77  32.08  0.03  0.001 to 0.07 --;

UNITED STATES PATENT AND TRADEMARK OFFICE
CERTIFICATE OF CORRECTION

PATENT NO. : 5,741,645
DATED : April 21, 1998
INVENTOR(S) : Harry T. Orr et al.

It is certified that error appears in the above-identified patent and that said Letters Patent is hereby corrected as shown below:

Column 17,
Line 23, delete all of Table 6 and insert the following

--Table 6.
STSs and YACs in 6p22-p23

| Probe | Primer set | YACs[a] | Annealing temp.[b] |
|---|---|---|---|
| D6S89 | cttgttcatctgccttgtgc (SEQ ID NO: 48) acctaagcgactgcctaaac (SEQ ID NO:49) | B126G2, B134D5, B172B3, B214D3, C5C12, 191D8, 299B3, 379C2, 468D12, 124G2, 511H11 | 55°C |
| AM10 (D6S335) | ttaaggaagtgttcacatcaggg (SEQ ID NO:50) aattgtgcttatgtcactggg (SEQ ID NO:51) | A23C3, A183C6, A250D5, B238F12, A91D2 | 55°C |
| A250D5-L (D6S337) | aattctggagagaggatgt (SEQ ID NO:52) tggttctttttttggtag (SEQ ID NO:53) | 195B5, 242C5, 475A6, 30F12 | 44°C |
| 64U | catcgtgttgtgtggtgaag (SEQ ID NO:54) ctcagacgctaaactcaagg (SEQ ID NO:55) | 492H3, 172B5, 227B1, 261H7 | 50°C |
| D6S288 | atgatccgtggtagtggc (SEQ ID NO:56) aggacctgttactgacgcc (SEQ ID NO:57) | 60H7, 351B10 | 55°C |
| D6S274 | ctcatctgttgaatggggat (SEQ ID NO:58) cttaaatgctatgccttccg (SEQ ID NO:59) | 486F9, 149H3, 42A5, 283B2, 320E12 | 55°C |
| FLB1 (D6S339) | tgcaaatccctcagttcact (SEQ ID NO:60) tgcttgactttgccatgttc (SEQ ID NO:61) | 140H2, 270D3, 274D12, 401D6, 57G3, 168F1 | 50°C |
| AM12 (D6S336) | atacccatacggatttgagg (SEQ ID NO:62) gcaacactatcaggctaagaatg (SEQ ID NO:63) | A71B3, 228A1, 193B3, 90A12, 539C11, 53G12, 35E8 | 55°C |
| 53G12-L | caaataccagcaactcaccagc (SEQ ID NO:64) ggttccttcagcatcctacattc (SEQ ID NO:65) | 3G6, 82G12, 98G5, 135F6, 198C8, 330G1 | 58°C |

UNITED STATES PATENT AND TRADEMARK OFFICE
CERTIFICATE OF CORRECTION

PATENT NO.   : 5,741,645
DATED        : April 21, 1998
INVENTOR(S)  : Harry T. Orr et al.

It is certified that error appears in the above-identified patent and that said Letters Patent is hereby corrected as shown below:

Column 17,
Table 6, footnote b, Line 3, delete "priemr" and insert -- primer --;

Column 21,
Table 7, entry for YAC 193B3, insert -- Y -- in Chimerism column;
Table 7, entry for YAC 228A1, insert -- Y -- in Chimerism column;
Table 7, entry for YAC 90A12, insert -- Y -- in Chimerism column;
Table 7, entry for YAC 35E8, insert -- N -- in Chimerism column;
Table 7, entry for YAC 53G12, insert -- N -- in Chimerism column;
Table 7, entry for YAC 135F6, insert -- N -- in Chimerism column;
Table 7, entry for YAC 82G12, insert -- N -- in Chimerism column;

Column 24,
Line 31, delete [α-$^{32}$p]dCTP and insert -- [α-$^{32P}$]dCTP --;

Column 50,
Line 5, delete second occurrence of "CAG" insert -- CAT --; and
Line 20, delete "CTCTGGCTTTCTTGGTG" and insert -- CTCTCGGCTTTCTTGGTG --.

Signed and Sealed this

Eighteenth Day of December, 2001

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 5,741,645
DATED         : April 21, 1998
INVENTOR(S)   : Harry T. Orr et al.

It is certified that error appears in the above-identified patent and that said Letters Patent is hereby corrected as shown below:

Column 17,
Line 23, delete all of Table 6 and insert the following:

--Table 6.
STSs and YACs in 6p22-p23

| Probe | Primer set | YACs[a] | Annealing temp.[b] |
|---|---|---|---|
| D6S89 | cttgttcatctgccttgtgc (SEQ ID NO: 48) acctaagcgactgcctaaac (SEQ ID NO:49) | B126G2, B134D5, B172B3, B214D3, C5C12, 191D8, 299B3, 379C2, 468D12, 124G2, 511H11 | 55°C |
| AM10 (D6S335) | ttaaggaagtgttcacatcaggg (SEQ ID NO:50) aattgtgcttatgtcactggg (SEQ ID NO:51) | A23C3, A183C6, A250D5, B238F12, A91D2 | 55°C |
| A250D5-L (D6S337) | aattctggagagaggatgt (SEQ ID NO:52) tggttctttttttggtag (SEQ ID NO:53) | 195B5, 242C5, 475A6, 30F12 | 44°C |
| 64U | catcgtgttgtgtggtgaag (SEQ ID NO:54) ctcagacgctaaactcaagg (SEQ ID NO:55) | 492H3, 172B5, 227B1, 261H7 | 50°C |
| D6S288 | atgatccgtggtagtggc (SEQ ID NO:56) aggacctgttactgacgcc (SEQ ID NO:57) | 60H7, 351B10 | 55°C |

UNITED STATES PATENT AND TRADEMARK OFFICE
CERTIFICATE OF CORRECTION

PATENT NO. : 5,741,645  
DATED : April 21, 1998  
INVENTOR(S) : Harry T. Orr et al.

Page 2 of 2

It is certified that error appears in the above-identified patent and that said Letters Patent is hereby corrected as shown below:

| D6S274 | ctcatctgttgaatggggat (SEQ ID NO:58)<br>cttaaatgctatgccttccg (SEQ ID NO:59) | 486F9, 149H3, 42A5, 283B2, 320E12 | 55°C |
|---|---|---|---|
| FLB1 (D6S339) | tgcaaatccctcagttcact (SEQ ID NO:60)<br>tgcttgactttgccatgttc (SEQ ID NO:61) | 140H2, 270D3, 274D12, 401D6, 57G3, 168F1 | 50°C |
| AM12 (D6S336) | atacccatacggatttgagg (SEQ ID NO:62)<br>gcaacactatcaggctaagaatg (SEQ ID NO:63) | A71B3, 228A1, 193B3, 90A12, 539C11, 53G12, 35E8 | 55°C |
| 53G12-L | caaataccagcaactcaccagc (SEQ ID NO:64)<br>ggttccttcagcatcctacattc (SEQ ID NO:65) | 3G6, 82G12, 98G5, 135F6, 198C8, 330G1 | 58°C |

Signed and Sealed this

Fifth Day of August, 2003

JAMES E. ROGAN  
*Director of the United States Patent and Trademark Office*

UNITED STATES PATENT AND TRADEMARK OFFICE
CERTIFICATE OF CORRECTION

PATENT NO. : 5,741,645
DATED : April 21, 1998
INVENTOR(S) : Harry T. Orr et al.

It is certified that error appears in the above-identified patent and that said Letters Patent is hereby corrected as shown below:

Column 17,
Line 23, delete all of Table 6 and insert the following:

--Table 6.

STSs and YACs in 6p22-p23

| Probe | Primer set | YACs[a] | Annealing temp.[b] |
|---|---|---|---|
| D6S89 | cttgttcatctgccttgtgc (SEQ ID NO:30) acctaagcgactgcctaaac (SEQ ID NO:31) | B126G2, B134D5, B172B3, B214D3, C5C12, 191D8, 299B3, 379C2, 468D12, 124G2, 511H11 | 55°C |
| AM10 (D6S335) | ttaaggaagtgttcacatcaggg (SEQ ID NO:32) aattgtgcttatgtcactggg (SEQ ID NO:33) | A23C3, A183C6, A250D5, B238F12, A91D2 | 55°C |
| A250D5-L (D6S337) | aattctggagagaggatgt (SEQ ID NO:34) tggttcttttttggtag (SEQ ID NO:35) | 195B5, 242C5, 475A6, 30F12 | 44°C |
| 64U | catcgtgttgtgtggtgaag (SEQ ID NO:36) ctcagacgctaaactcaagg (SEQ ID NO:37) | 492H3, 172B5, 227B1, 261H7 | 50°C |
| D6S288 | atgatccgtggtagtggc (SEQ ID NO:38) aggacctgttactgacgcc (SEQ ID NO:39) | 60H7, 351B10 | 55°C |

UNITED STATES PATENT AND TRADEMARK OFFICE
CERTIFICATE OF CORRECTION

PATENT NO.   : 5,741,645
DATED        : April 21, 1998
INVENTOR(S)  : Harry T. Orr et al.

It is certified that error appears in the above-identified patent and that said Letters Patent is hereby corrected as shown below:

| | | | |
|---|---|---|---|
| D6S274 | ctcatctgttgaatgggggat (SEQ ID NO:40) cttaaatgctatgccttccg (SEQ ID NO:41) | 486F9, 149H3, 42A5, 283B2, 320E12 | 55°C |
| FLB1 (D6S339) | tgcaaatccctcagttcact (SEQ ID NO:42) tgcttgactttgccatgttc (SEQ ID NO:43) | 140H2, 270D3, 274D12, 401D6, 57G3, 168F1 | 50°C |
| AM12 (D6S336) | atacccatacggatttgagg (SEQ ID NO:44) gcaacactatcaggctaagaatg (SEQ ID NO:45) | A71B3, 228A1, 193B3, 90A12, 539C11, 53G12, 35E8 | 55°C |
| 53G12-L | caaataccagcaactcaccagc (SEQ ID NO:46) ggttccttcagcatcctacattc (SEQ ID NO:47) | 3G6, 82G12, 98G5, 135F6, 198C8, 330G1 | 58°C |

This certificate supersedes Certificate of Correction issued August 5, 2003.

Signed and Sealed this

Twentieth Day of January, 2004

JON W. DUDAS
*Acting Director of the United States Patent and Trademark Office*

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 3366 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
TTTTGAAACT TGCAGAGAAC AGGATTATTT CTGGCGGCCT CTGCTGAGTT GGCGTGTGTG      60
TGTGTGTTTG TGTGTGTGTG TATTAGGGAG AGGAAATCGT AGGTCCAGTG TGGACCCAGA     120
GCTAAGGGGA ATCTTGGAGA GTAGTGGCTC TGGCAGATGA GGATTCAGAA ATCGAGTGCA     180
AGGACTGTTC TGGACTTTCA CTGCTAACCT GCTTTTTCTC AGTGCCTGGC TCTGAGGGCA     240
GGGTCCAGCT GGTGTCATGC TCTCCAAGGG CTTCATTTTA TGTTCCAGCC AGGCAAAGGA     300
GAGGTGAGAA ATGGAACCAA CATTTCTGAA AAGGAAATTT AAGAACTGCA TCATCTGCCC     360
TTGAAGAAGA AAAGGAGAAA AAAAAACAGG AGAGAGGGTA TTGAGAACAT CTTAGGGGAG     420
TTGTTAACTC CATTAAAAAA TATATGTGTT ACAGTGTTCA CTTGCCCAGT GTCTTCATAA     480
TCTTCCTTTA TAATGTGCAG CTGCCACGGC TAGTGTTTTT GTTTTGTTG TTGTTGTTTT      540
GTTTCGTTTT TGGAGACAGA GTGTCGCTCT GTTGCCCAGG CTGGAGTACA ATGGTGCAAT     600
CTCGGCTCAC TGCAACCTCT GCCTCCTGGG TTCAAGCAAT TCTCCTGCCT CAGCCTCTCA     660
AGTAGCTGGG ACTACAGCCG TGTGCCAGCT AATGTTACAC CAGGCTAAAT TTGTTTTTTA     720
TTTTTTATTT TTGGTAGAGA CGGGGTTTCA CCATGTTAGC CAGGATGGTC TTAATCTCCT     780
GACCTCGTGA TCTGCCTGCC TCGGCCTCCC AAAGTGTTGG CTAGTGTTTT CTCTGCTTCA     840
GTGCTTGGGG TATGATTGGG TTATGGGAGT TCACACCGAG TCCAGGGCCT AGTCTTAATC     900
TTGCCAAAGA TGTTCTTTCC CCGGTGCTCA TGTTCTGATG TCCTTTCCCT CCTTCCCTTT     960
CTCCTCCCTT TCCTTTTCCC TTTGTCACTG CCCTCTTCCC TTTCCCAGCA TCCAGAGCTG    1020
CTGTTGGCGG ATTGTACCCA CGGGGAGATG ATTCCTCATG AAGAGCCTGG ATCCCCTACA    1080
GAAATCAAAT GTGACTTTCC GTTTATCAGA CTAAAATCAG AGCCATCCAG AACAGTGAAA    1140
CAGTCACCGT GGAGGGGGGA CGGCGAAAAA TGAAATCCAA CCAAGAGCGG AGCAACGAAT    1200
GCCTGCCTCC CAAGAAGCGC GAGATCCCCG CCACCAGCCG GTCCTCGGAG GAGAAGGCCC    1260
CTACCCTGAC CCAGCGACAA CCACCGGGTG GAGGGCACAG CATTGGCTCC CGGGCAACCC    1320
TGGTGGCCGG GGCCACGGGG GCGGGAGGCA TGGGCCGGCA GGGACCTCGG TGGAGCTTGG    1380
TTTACAACAG GGAATAGGTT TACACAAAGC ATTGTCCACA GGGCTGGACT ACTCCCCGCC    1440
CAGCGCTCCC AGGTCTGTCC CCGTGGCCAC CACGCTGCCT GCCGCGTACG CCACCCCGCA    1500
GCCAGGGACC CCGGTGTCCC CCGTGCAGTA CGCTCACCTG CCGCACACCT TCCAGTTCAT    1560
TGGGTCCTCC CAATACAGTG GAACCTATGC CAGCTTCATC CCATCACAGC TGATCCCCCC    1620
AACCGCCAAC CCCGTCACCA GTGCAGTGGC CTCGGCGCAG GGGCCACCAC TCCATCCCAG    1680
CGCTCCCAGC TGGAGGCCTA TTCCACTCTG CTGGCCAACA TGGGCAGTCT GAGCCAGACG    1740
CCGGGACACA AGGCTGAGCA GCAGCAGCAG CAGCAGCAGC AGCAGCAGCA GCAGCATCAG    1800
```

```
CATCAGCAGC  AGCAGCAGCA  GCAGCAGCAG  CAGCAGCAGC  AGCAGCAGCA  CCTCAGCAGG    1860

GCTCCGGGGC  TCATCACCCC  GGGTCCCCCC  CAACCAGCCC  AGCAGAACCA  GTACGTCCAC    1920

ATTTCCAGTT  CTCCGCAGAA  CACCGGCCGC  ACCGCCTCTC  CTCCGGCCAT  CCCCGTCCAC    1980

CTCCACCCCC  ACCAGACGAT  GATCCCACAC  ACGCTCACCC  TGGGGCCCCC  CTCCCAGGTC    2040

GTCATGCAAT  ACGCCGACTC  CGGCAGCCAC  TTTGTCCCTC  GGGAGGCCAC  CAAGAAAGCC    2100

GAGAGCAGCC  GGCTGCAGCA  GGCCATCCAG  GCCAAGGAGG  TCCTGAACGG  TGAGATGGAG    2160

AAGAGCCGGC  GGTACGGGGC  CCCGTCCTCA  GCCGACCTGG  GCCTGGGCAA  GGCAGGCGGC    2220

AAGTCGGTTC  CTCACCCGTA  CGAGTCCAGG  CACGTGGTGG  TCCACCCGAG  CCCCTCAGAC    2280

TACAGCAGTC  GTGATCCTTC  GGGGGTCCGG  GCCTCTGTGA  TGGTCCTGCC  CAACAGCAAC    2340

ACGCCCGCAG  CTGACCTGGA  GGTGCAACAG  GCCACTCATC  GTGAAGCCTC  CCCTTCTACC    2400

CTCAACGACA  AAAGTGGCCT  GCATTTAGGG  AAGCCTGGCC  ACCGGTCCTA  CGCGCTCTCA    2460

CCCCACACGG  TCATTCAGAC  CACACACAGT  GCTTCAGAGC  CACTCCCGGT  GGACTGCCAG    2520

CCACGGCCTT  CTACGCAGGG  ACTCAACCCC  CTGTCATCGG  CTACCTGAGC  GGCCAGCAGC    2580

AAGCAATCAC  CTACGCCGGC  AGCCTGCCCC  AGCACCTGGT  GATCCCCGGC  ACACAGCCCC    2640

TGCTCATCCC  GGTCGGCAGC  ACTGACATGG  AAGCGTCGGG  GGCAGCCCCG  GCCATAGTCA    2700

CGTCATCCCC  CCAGTTTGCT  GCAGTGCCTC  ACACGTTCGT  CACCACCGCC  CTTCCCAAGA    2760

GCGAGAACTT  CAACCCTGAG  GCCCTGGTCA  CCCAGGCCGC  CTACCCAGCC  ATGGTGCAGG    2820

CCCAGATCCA  CCTGCCTGTG  GTGCAGTCCG  TGGCCTCCCC  GGCGGCGGCT  CCCCCTACGC    2880

TGCCTCCCTA  CTTCATGAAA  GGCTCCATCA  TCCAGTTGGC  CAACGGGGAG  CTAAAGAAGG    2940

TGGAAGACTT  AAAACAGAAG  ATTTCATCCA  GAGTGCAGAG  ATAAGCAACG  ACCTGAAGAT    3000

CGACTCCAGC  ACCGTAGAGA  GGATTGAAGA  CAGCCATAGC  CCGGGCGTGG  CCGTGATACA    3060

GTTCGCCGTC  GGGGAGCACC  GAGCCCAGGT  AACGTTAGCC  AGGGTGGCAC  AGGGATGGGA    3120

CACCATACCG  TGATGCCATC  ATCATCTCCT  GGCAAGACGA  ATTGCTTCTA  TGAGGCAGGA    3180

TTAAGGGTTC  TCGGGTACAC  CTAGACCTTA  GACTCGGCCT  TTCCCAACTG  CGTTCTCTAG    3240

AAAAAATAAG  CCCCATTTCC  CCGTGATCTC  TGCTGTGTGT  AATGAATTAA  CCTCCATGCA    3300

TGGAGAGTGG  GGCTAGTTAT  GGAGTCCTTG  AGACAATCCA  GAAACTCACC  ACTCTCGTTA    3360

TTTTTT                                                                   3366
```

( 2 ) INFORMATION FOR SEQ ID NO:2:

( i ) SEQUENCE CHARACTERISTICS:
        ( A ) LENGTH: 195 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
CAGCAGCAGC  AGCAGCAGCA  GCAGCAGCAG  CAGCAGCAGC  AGCAGCAGCA  GCAGCAGCAG     60

CAGCAGCAGC  AGCAGCAGCA  GCAGCAGCAG  CAGCAGCAGC  AGCAGCAGCA  GCAGCAGCAG    120

CAGCAGCAGC  AGCAGCAGCA  GCAGCAGCAG  CAGCAGCAGC  AGCAGCAGCA  CCTCAGCAGG    180

GCTCCGGGGC  TCATC                                                        195
```

( 2 ) INFORMATION FOR SEQ ID NO:3:

( i ) SEQUENCE CHARACTERISTICS:
        ( A ) LENGTH: 234 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:3:

| | | | | | | |
|---|---|---|---|---|---|---|
| CAGCAGCAGC | AGCAGCAGCA | GCAGCAGCAG | CAGCAGCAGC | AGCAGCAGCA | GCAGCAGCAG | 60 |
| CAGCAGCAGC | AGCAGCAGCA | GCAGCAGCAG | CAGCAGCAGC | AGCAGCAGCA | GCAGCAGCAG | 120 |
| CAGCAGCAGC | AGCAGCAGCA | GCAGCAGCAG | CAGCAGCAGC | AGCAGCAGCA | GCAGCAGCAG | 180 |
| CAGCAGCAGC | AGCAGCAGCA | GCAGCAGCAC | CTCAGCAGGG | CTCCGGGGCT | CATC | 234 |

(2) INFORMATION FOR SEQ ID NO:4:

(i) SEQUENCE CHARACTERISTICS:
(A) LENGTH: 168 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:4:

| | | | | | | |
|---|---|---|---|---|---|---|
| CAGCAGCAGC | AGCAGCAGCA | GCAGCAGCAG | CAGCAGCAGC | AGCAGCAGCA | GCAGCAGCAG | 60 |
| CAGCAGCAGC | AGCAGCAGCA | GCAGCAGCAG | CAGCAGCAGC | AGCAGCAGCA | GCAGCAGCAG | 120 |
| CAGCAGCAGC | AGCAGCAGCA | GCACCTCAGC | AGGGCTCCGG | GGCTCATC | | 168 |

(2) INFORMATION FOR SEQ ID NO:5:

(i) SEQUENCE CHARACTERISTICS:
(A) LENGTH: 171 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:5:

| | | | | | | |
|---|---|---|---|---|---|---|
| CAGCAGCAGC | AGCAGCAGCA | GCAGCAGCAG | CAGCAGCAGC | AGCAGCAGCA | GCAGCAGCAG | 60 |
| CAGCAGCAGC | AGCAGCAGCA | GCAGCAGCAG | CAGCAGCAGC | AGCAGCAGCA | GCAGCAGCAG | 120 |
| CAGCAGCAGC | AGCAGCAGCA | GCAGCACCTC | AGCAGGGCTC | CGGGGCTCAT | C | 171 |

(2) INFORMATION FOR SEQ ID NO:6:

(i) SEQUENCE CHARACTERISTICS:
(A) LENGTH: 154 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

| | | | | | | |
|---|---|---|---|---|---|---|
| TGAGCAGCAG | CAGCAGCAGC | AGCAGCAGCA | GCAGCAGCAG | CAGCAGCAGC | AGCAGCAGCA | 60 |
| GCAGCAGCAG | CAGCAGCAGC | AGCAGCAGCA | GCAGCAGCAG | CAGCAGCAGC | AGCAGCAGCA | 120 |
| GCAGCAGCAG | CAGCAGCAGC | AGCAGCAGCA | GCAG | | | 154 |

(2) INFORMATION FOR SEQ ID NO:7:

(i) SEQUENCE CHARACTERISTICS:
(A) LENGTH: 506 base pairs
(B) TYPE: nucleic acid
(C) STRANDEDNESS: single ( D ) TOPOLOGY: linear ( i i ) MOLECULE TYPE: DNA ( x i ) SEQUENCE DESCRIPTION: SEQ ID NO:7:

| | | | | | | |
|---|---|---|---|---|---|---|
| GATCCCCCCA | ACCGCCAACC | CCGTCACCAG | TGCAGTGGCC | TCGGCGCAGG | GGCCACCACT | 60 |
| CCATCCCAGC | CCTCCCAGCT | GGAGGCCTAT | TCCACTCTGC | TGGCCAACAT | GGGCAGTCTG | 120 |
| AGCCAGACGC | CGGGACACAA | GGCTGAGCAG | CAGCAGCAGC | AGCAGCAGCA | GCAGCAGCAG | 180 |
| CAGCATCAGC | ATCAGCAGCA | GCAGCAGCAG | CAGCAGCAGC | AGCAGCAGCA | CCAGCAGCAC | 240 |
| CTCAGCAGGG | CTCCGGGGCT | CATCACCCCG | GGTCCCCCCC | ACCAGCCCAG | CAGAACCAGT | 300 |
| ACGTCCACAT | TTCCAGTTCT | CCGCAGAACA | CCGGCCGCAC | CGCCTCTCCT | CCGGCCATCC | 360 |
| CCGTCCACCT | CCACCCCCAC | CAGACGATGA | TCCACACAC | GCTCACCCTG | GGGCCCCCCT | 420 |
| CCCAGGTCGT | CATGCAATAC | GCCGACTCCG | GCAGCCACTT | TGTCCCTCGG | GAGGCCACCA | 480 |
| AGAAAGCCGA | GAGCAGCCGG | CTGCAG | | | | 506 |

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CCGGAGCCCT GCTGAGGT           18

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CCAGACGCCG GGACAC           16

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

AACTGGAAAT GTGGACGTAC           20

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

CAACATGGGC AGTCTGAG							18

( 2 ) INFORMATION FOR SEQ ID NO:12:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:12:

CCACCACTCC ATCCCAGC							18

( 2 ) INFORMATION FOR SEQ ID NO:13:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:13:

TGCTGGGCTG GTGGGGGG							18

( 2 ) INFORMATION FOR SEQ ID NO:14:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:14:

CTCTCGGCTT TCTTGGTG							18

( 2 ) INFORMATION FOR SEQ ID NO:15:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:15:

GTACGTCCAC ATTTCCAGTT							20

( 2 ) INFORMATION FOR SEQ ID NO:16:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:16:

AGGAGTGAGC CACCGCACCC AGCC						24

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

CCCGGATCCT GTGTGTGTGT GTGTGTG                                  27

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

CCCGGATCCA CACACACACA CACACAC                                  27

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

AAGTCAGCCT CTACTCTTTG TTGA                                      24

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

CTTGGAGCAG TCTGTAGGGA G                                          21

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

TGAAGTGATG TGCTCTGTTC                                            20

( 2 ) INFORMATION FOR SEQ ID NO:22:

( i ) SEQUENCE CHARACTERISTICS:
        ( A ) LENGTH: 20 base pairs
        ( B ) TYPE: nucleic acid (C) STRANDEDNESS: single
(D) TOPOLOGY: linear (ii) MOLECULE TYPE: DNA (xi) SEQUENCE DESCRIPTION: SEQ ID NO:22:

AAAGGGGTAG AGGAAATGAG　　　　　　　　　　　　　　　　　　　　20

(2) INFORMATION FOR SEQ ID NO:23:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:23:

AGGAGAGGGG TCATGAGTTG　　　　　　　　　　　　　　　　　　　　20

(2) INFORMATION FOR SEQ ID NO:24:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:24:

GGCTCATGAA TACATTACAT GAAG　　　　　　　　　　　　　　　　　24

(2) INFORMATION FOR SEQ ID NO:25:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:25:

CTCATTCACC TTAGAGACAA ATGGATAG　　　　　　　　　　　　　　28

(2) INFORMATION FOR SEQ ID NO:26:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:26:

ATGGTATAGG GATTTNCCA AACCTG　　　　　　　　　　　　　　　26

(2) INFORMATION FOR SEQ ID NO:27:

(i) SEQUENCE CHARACTERISTICS:
  (A) LENGTH: 54 base pairs
  (B) TYPE: nucleic acid
  (C) STRANDEDNESS: single
  (D) TOPOLOGY: linear (ii) MOLECULE TYPE: DNA ( x i ) SEQUENCE DESCRIPTION: SEQ ID NO:27:

CACACACACA CACACACACA CACACACACA CATACACACA CACACACACA CACA  54

( 2 ) INFORMATION FOR SEQ ID NO:28:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

GAGAATGACA GAGAGAGAGA GAGAGAGAGA GA  32

( 2 ) INFORMATION FOR SEQ ID NO:29:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

GAGAAAGAGA GAGAGAGAGT GAGTGTGTGT GTGTGTGTGT GTGTGTGTGT GTGTATGTGT  60

GTGTGT  66

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

CTTGTTCATC TGCCTTGTGC  20

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

ACCTAAGCGA CTGCCTAAAC  20

( 2 ) INFORMATION FOR SEQ ID NO:32:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

TTAAGGAAGT GTTCACATCA GGG  23

( 2 ) INFORMATION FOR SEQ ID NO:33:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

AATTGTGCTT ATGTCACTGG G    21

( 2 ) INFORMATION FOR SEQ ID NO:34:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

AATTCTGGAG AGGATGT    17

( 2 ) INFORMATION FOR SEQ ID NO:35:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

TGGTTCTTTT TTTGGTAG    18

( 2 ) INFORMATION FOR SEQ ID NO:36:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

CATCGTGTTG TGTGGTGAAG    20

( 2 ) INFORMATION FOR SEQ ID NO:37:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

CTCAGACGCT AAACTCAAGG    20

( 2 ) INFORMATION FOR SEQ ID NO:38:

( i ) SEQUENCE CHARACTERISTICS:

( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:38:

ATGATCCGTG GTAGTGGC                                                                        1 8

( 2 ) INFORMATION FOR SEQ ID NO:39:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:39:

AGGACCTGT TACTGACGCC                                                                           1 9

( 2 ) INFORMATION FOR SEQ ID NO:40:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:40:

CTCATCTGTT GAATGGGGAT                                                                      2 0

( 2 ) INFORMATION FOR SEQ ID NO:41:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:41:

CTTAAATGCT ATGCCTTCCG                                                                          2 0

( 2 ) INFORMATION FOR SEQ ID NO:42:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:42:

TGCAAATCCC TCAGTTCACT                                                                      2 0

( 2 ) INFORMATION FOR SEQ ID NO:43:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear (i i) MOLECULE TYPE: DNA (x i) SEQUENCE DESCRIPTION: SEQ ID NO:43:

TGCTTGACTT TGCCATGTTC 20

(2) INFORMATION FOR SEQ ID NO:44:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:44:

ATACCCATAC GGATTTGAGG 20

(2) INFORMATION FOR SEQ ID NO:45:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:45:

GCAACACTAT CAGGCTAAGA ATG 23

(2) INFORMATION FOR SEQ ID NO:46:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:46:

CAAATACCAG CAACTCACCA GC 22

(2) INFORMATION FOR SEQ ID NO:47:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:47:

GGTTCCTTCA GCATCCTACA TTC 23